(12) United States Patent
Legeai-Mallet et al.

(10) Patent No.: US 9,931,341 B2
(45) Date of Patent: Apr. 3, 2018

(54) ANTAGONIST OF THE FIBROBLAST GROWTH FACTOR RECEPTOR 3 (FGFR3) FOR USE IN THE TREATMENT OR THE PREVENTION OF SKELETAL DISORDERS LINKED WITH ABNORMAL ACTIVATION OF FGFR3

(71) Applicants: INSTITUT NATIONAL DE LA SANTE ET DE LA RECHERCHE MEDICALE (INSERM), Paris (FR); UNIVERSITE PARIS DESCARTES, Paris (FR); CENTRE NATIONAL DE LA RECHERCHE SCIENTIFIQUE (CNRS), Paris (FR); ASSISTANCE PUBLIQUE-HOPITAUX DE PARIS, Paris (FR); UNIVERSITE PARIS DIDEROT—PARIS 7, Paris (FR); IMAGINE, Paris (FR)

(72) Inventors: Laurence Legeai-Mallet, Paris (FR); Arnold Munnich, Paris (FR); Patricia Busca, Paris (FR); Florent Barbault, Paris (FR)

(73) Assignees: INSTITUT NATIONAL DE LA SANTE ET DE LA RECHERCHE MEDICALE (INSERM), Paris (FR); UNIVERSITE PARIS DESCARTES, Paris (FR); CENTRE NATIONAL DE LA RECHERCHE SCIENTIFIQUE (CNRS), Paris (FR); ASSITANCE PUBLIQUE HOPITAUX DE PARIS, Paris (FR); UNIVERSITE PARIS DIDEROT-PARIS 7, Paris (FR); IMAGINE, Paris (FR)

( * ) Notice: Subject to any disclaimer, the term of this patent is extended or adjusted under 35 U.S.C. 154(b) by 0 days.

(21) Appl. No.: 14/844,041

(22) Filed: Sep. 3, 2015

(65) Prior Publication Data
US 2016/0051549 A1 Feb. 25, 2016

Related U.S. Application Data

(63) Continuation of application No. 14/364,320, filed as application No. PCT/EP2012/075294 on Dec. 12, 2012, now abandoned.

(30) Foreign Application Priority Data

Dec. 12, 2011 (WO) .................. PCT/IB2011/003254

(51) Int. Cl.
| | | |
|---|---|---|
| A61K 31/497 | (2006.01) |
| A61K 31/506 | (2006.01) |
| C08J 5/18 | (2006.01) |
| C08L 51/04 | (2006.01) |
| B32B 27/30 | (2006.01) |
| B29C 47/00 | (2006.01) |
| B29K 25/00 | (2006.01) |
| B29K 35/00 | (2006.01) |
| B29K 201/00 | (2006.01) |
| B29L 31/00 | (2006.01) |
| C08L 25/06 | (2006.01) |

(52) U.S. Cl.
CPC ........ A61K 31/506 (2013.01); B29C 47/0004 (2013.01); B29C 47/0054 (2013.01); B32B 27/302 (2013.01); C08J 5/18 (2013.01); C08L 51/04 (2013.01); B29K 2025/06 (2013.01); B29K 2035/00 (2013.01); B29K 2201/00 (2013.01); B29L 2031/712 (2013.01); B32B 2262/06 (2013.01); B32B 2270/00 (2013.01); B32B 2439/70 (2013.01); C08J 2325/06 (2013.01); C08J 2401/00 (2013.01); C08J 2401/02 (2013.01); C08J 2425/06 (2013.01); C08J 2425/08 (2013.01); C08J 2447/00 (2013.01); C08L 25/06 (2013.01); C08L 2203/30 (2013.01); C08L 2205/02 (2013.01); C08L 2205/025 (2013.01); C08L 2205/03 (2013.01); C08L 2205/035 (2013.01); C08L 2205/16 (2013.01)

(58) Field of Classification Search
CPC .. A61K 31/506; A61K 31/519; A61K 38/177; A61K 38/179
See application file for complete search history.

(56) References Cited

FOREIGN PATENT DOCUMENTS

| EP | 1 964 837 A1 | 9/2008 |
|---|---|---|
| WO | 02/102973 A2 | 12/2002 |
| WO | 2010/022169 A1 | 2/2010 |
| WO | 00/68424 A2 | 11/2010 |

OTHER PUBLICATIONS

Le Corre et al., "Synthesis and biological evaluation of a triazole-based library of pyrido[2,3-d]pyrimidines as FGFR3 tyrosine kinase inhibitors", Organic and Biomolecular Chemistry, May 7, 2010, pp. 2164-2173, vol. 8, No. 9.
Krejci et al., "NF449 is a Novel Inhibitor of Fibroblast Growth Factor Receptor 3 (FGFR3) Signaling Active in Chondrocytes and Multiple Myeloma Cells", Journal of Biological Chemistry, Jul. 2010, pp. 20644-20653, vol. 285, No. 27.
Guagnano et al., "Discovery of 3-(2,6-Dichloro-3,5-deimthoxy-phenyl)-1-{6-[4-(4-ethyl-piperazin-1-yl)-phenylamino]-pyrimidin-4-yl}-1-methyl-urea (NVP-BGJ398), A Potent and Selective Inhibitor of the Fibroblast Growth Factor Receptor Family of Receptor Tyrosine Kinase", Journal of Medicinal Chemistry, Oct. 27, 2011, pp. 7066-7083, vol. 54, No. 20, American Chemical Society, US.
Jonquoy et al., "A novel tyrosine kinase inhibitor restores chondrocyte differentiation and promotes bone growth in a gain of function Fgfr3 mouse model", Hum Mol Genet, Nov. 9, 2011.

*Primary Examiner* — Jean Cornet
(74) *Attorney, Agent, or Firm* — Whitham, Curtis & Cook

(57) ABSTRACT

The present invention relates to the treatment or prevention of skeletal disorders, in particular skeletal diseases, developed by patients that display abnormal increased activation of the fibroblast growth factor receptor 3 (FGFR3), in particular by expression of a constitutively activated mutant of FGFR3.

1 Claim, 7 Drawing Sheets

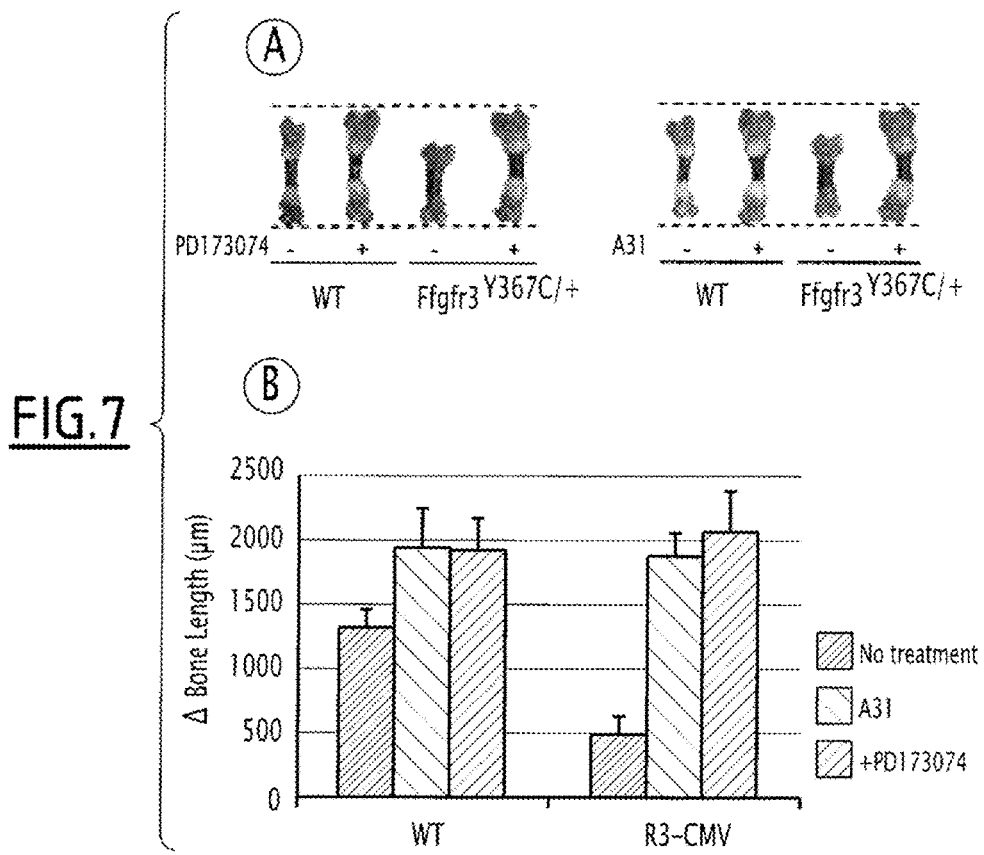
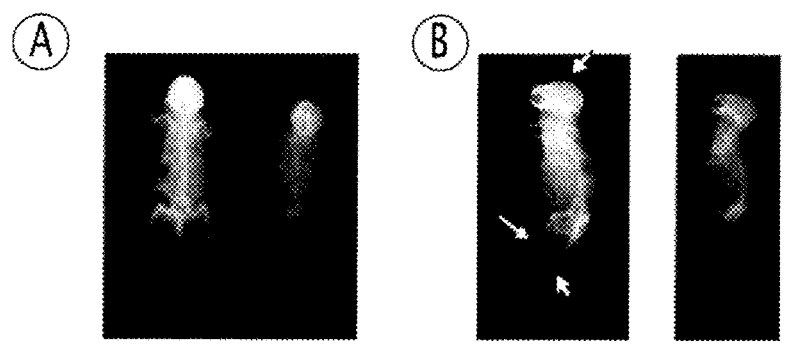
FIG.8

SEQUENCE LISTING

<160> NUMBER OF SEQ ID NOS: 1

<210> SEQ ID NO 1
<211> LENGTH: 806
<212> TYPE: PRT
<213> ORGANISM: Homo sapiens

<400> SEQUENCE: 1

Met Gly Ala Pro Ala Cys Ala Leu Ala Leu Cys Val Ala Val Ala Ile
1               5                   10                  15

```
Val Ala Gly Ala Ser Ser Glu Ser Leu Gly Thr Glu Gln Arg Val Val
             20                  25                  30

Gly Arg Ala Ala Glu Val Pro Gly Pro Glu Pro Gly Gln Gln Glu Gln
             35                  40                  45

Leu Val Phe Gly Ser Gly Asp Ala Val Glu Leu Ser Cys Pro Pro Pro
             50                  55                  60

Gly Gly Gly Pro Met Gly Pro Thr Val Trp Val Lys Asp Gly Thr Gly
 65                  70                  75                  80

Leu Val Pro Ser Glu Arg Val Leu Val Gly Pro Gln Arg Leu Gln Val
                 85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
            115                 120                 125

Pro Ser Ser Gly Asp Asp Glu Asp Gly Glu Asp Glu Ala Glu Asp Thr
            130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
            180                 185                 190

Arg Glu Phe Arg Gly Glu His Arg Ile Gly Gly Ile Lys Leu Arg His
            195                 200                 205

Gln Gln Trp Ser Leu Val Met Glu Ser Val Val Pro Ser Asp Arg Gly
            210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
            260                 265                 270

Phe His Cys Lys Val Tyr Ser Asp Ala Gln Pro His Ile Gln Trp Leu
            275                 280                 285

Lys His Val Glu Val Asn Gly Ser Lys Val Gly Pro Asp Gly Thr Pro
            290                 295                 300

Tyr Val Thr Val Leu Lys Thr Ala Gly Ala Asn Thr Thr Asp Lys Glu
305                 310                 315                 320

Leu Glu Val Leu Ser Leu His Asn Val Thr Phe Glu Asp Ala Gly Glu
                325                 330                 335

Tyr Thr Cys Leu Ala Gly Asn Ser Ile Gly Phe Ser His His Ser Ala
            340                 345                 350

Trp Leu Val Val Leu Pro Ala Glu Glu Glu Leu Val Glu Ala Asp Glu
            355                 360                 365

Ala Gly Ser Val Tyr Ala Gly Ile Leu Ser Tyr Gly Val Gly Phe Phe
            370                 375                 380

Leu Phe Ile Leu Val Val Ala Ala Val Thr Leu Cys Arg Leu Arg Ser
385                 390                 395                 400

Pro Pro Lys Lys Gly Leu Gly Ser Pro Thr Val His Lys Ile Ser Arg
                405                 410                 415
```

```
Phe Pro Leu Lys Arg Gln Val Ser Leu Glu Ser Asn Ala Ser Met Ser
            420                 425                 430

Ser Asn Thr Pro Leu Val Arg Ile Ala Arg Leu Ser Ser Gly Glu Gly
            435                 440                 445

Pro Thr Leu Ala Asn Val Ser Glu Leu Glu Leu Pro Ala Asp Pro Lys
            450                 455                 460

Trp Glu Leu Ser Arg Ala Arg Leu Thr Leu Gly Lys Pro Leu Gly Glu
465                 470                 475                 480

Gly Cys Phe Gly Gln Val Val Met Ala Glu Ala Ile Gly Ile Asp Lys
                    485                 490                 495

Asp Arg Ala Ala Lys Pro Val Thr Val Ala Val Lys Met Leu Lys Asp
            500                 505                 510

Asp Ala Thr Asp Lys Asp Leu Ser Asp Leu Val Ser Glu Met Glu Met
            515                 520                 525

Met Lys Met Ile Gly Lys His Lys Asn Ile Ile Asn Leu Leu Gly Ala
            530                 535                 540

Cys Thr Gln Gly Gly Pro Leu Tyr Val Leu Val Glu Tyr Ala Ala Lys
545                 550                 555                 560

Gly Asn Leu Arg Glu Phe Leu Arg Ala Arg Arg Pro Pro Gly Leu Asp
                    565                 570                 575

Tyr Ser Phe Asp Thr Cys Lys Pro Pro Glu Glu Gln Leu Thr Phe Lys
            580                 585                 590

Asp Leu Val Ser Cys Ala Tyr Gln Val Ala Arg Gly Met Glu Tyr Leu
            595                 600                 605

Ala Ser Gln Lys Cys Ile His Arg Asp Leu Ala Ala Arg Asn Val Leu
            610                 615                 620

Val Thr Glu Asp Asn Val Met Lys Ile Ala Asp Phe Gly Leu Ala Arg
625                 630                 635                 640

Asp Val His Asn Leu Asp Tyr Tyr Lys Lys Thr Thr Asn Gly Arg Leu
                    645                 650                 655

Pro Val Lys Trp Met Ala Pro Glu Ala Leu Phe Asp Arg Val Tyr Thr
            660                 665                 670

His Gln Ser Asp Val Trp Ser Phe Gly Val Leu Leu Trp Glu Ile Phe
            675                 680                 685

Thr Leu Gly Gly Ser Pro Tyr Pro Gly Ile Pro Val Glu Glu Leu Phe
            690                 695                 700

Lys Leu Leu Lys Glu Gly His Arg Met Asp Lys Pro Ala Asn Cys Thr
705                 710                 715                 720

His Asp Leu Tyr Met Ile Met Arg Glu Cys Trp His Ala Ala Pro Ser
                    725                 730                 735

Gln Arg Pro Thr Phe Lys Gln Leu Val Glu Asp Leu Asp Arg Val Leu
            740                 745                 750

Thr Val Thr Ser Thr Asp Glu Tyr Leu Asp Leu Ser Ala Pro Phe Glu
            755                 760                 765

Gln Tyr Ser Pro Gly Gly Gln Asp Thr Pro Ser Ser Ser Ser Ser Gly
            770                 775                 780

Asp Asp Ser Val Phe Ala His Asp Leu Leu Pro Pro Ala Pro Pro Ser
785                 790                 795                 800

Ser Gly Gly Ser Arg Thr
                    805
```

ANTAGONIST OF THE FIBROBLAST GROWTH FACTOR RECEPTOR 3 (FGFR3) FOR USE IN THE TREATMENT OR THE PREVENTION OF SKELETAL DISORDERS LINKED WITH ABNORMAL ACTIVATION OF FGFR3

FIELD OF THE INVENTION

The present invention relates to the treatment or prevention of skeletal disorders, in particular skeletal diseases and craniosynostosis, developed by patients that display abnormal increased activation of the fibroblast growth factor receptor 3 (FGFR3), in particular by expression of a constitutively activated mutant of FGFR3.

BACKGROUND

Skeletal development in humans is regulated by numerous growth factors. Among them Fibroblast Growth Factor Receptor 3 (FGFR3) has been described as both a negative and a positive regulator of endochondral ossification.

The FGFR3 gene, which is located on the distal short arm of chromosome 4, encodes a 806 amino acid protein precursor (fibroblast growth factor receptor 3 isoform 1 precursor; SEQ ID NO: 1).

The FGFR3 protein belongs to the receptor-tyrosine kinase family. This family comprises receptors FGFR1, FGFR2, FGFR3 and FGFR4 that respond to fibroblast growth factor (FGF) ligands. These structurally related proteins exhibit an extracellular domain composed of three immunoglobin-like domains which form the ligand-binding domain, an acid box, a single transmembrane domain and an intracellular split tyrosine kinase domain. Although to date the physiological ligand(s) for FGFR3 is (are) not known, like other FGFRs, it is activated by FGF ligands. Binding of one of the 22 FGFs induces receptor dimerization and autophosphorylation of tyrosine residues in the cytoplasmic domain. The phosphorylated tyrosine residues are required for activation of the signaling pathways. The most relevant tyrosines are Y648, Y647, located in the activation loop.

Several signaling pathways have been described downstream of FGFR3 activation, including the ERK and p38 MAP kinase pathways (Legeai-Mallet et al., J Biol Chem, 273: 13007-13014, 1998; Murakami at al., Genes Dev, 18: 290-305, 2004; Matsushita et al., Hum Mol Genet, 18: 227-240, 2009; Krejci et al., J Cell Sci, 121: 272-281, 2008) and the signal transducer and activation of transcription (STAT) pathway (Su, W. C. at al., Nature, 386: 288-292, 1997; Legeai-Mallet et al., Bone, 34: 26-3, 2004; Li, C. at al., Hum Mol Genet, 8: 35-44, 1999). Others pathways in endochondral bone growth have been identified such as the phosphoinositide 3 kinase-AKT (Ulici, V. et al., Bone, 45: 1133-1145, 2009) and protein kinase C pathways. The degradation of mutant receptors is disturbed as demonstrated by higher levels of FGFR3 mutant receptors at the cell surface (Monsonego-Ornan et al., Mol Cell Biol, 20: 516-522, 2000; Monsonego-Ornan et al., FEBS Lett, 528: 83-89, 2002; Delezoide et al., Hum Mol Genet, 6: 1899-1906, 1997), and disruption of c-Cbl-mediated ubiquitination (Cho, J. Y. et al., Proc Natl Aced Sci USA, 101: 609-614, 2004). FGFR3 mutations disrupt the formation of glycosylated isoforms of the receptor and impeded its trafficking (Gibbs et al., Biochim Biophys Acta, 1773: 502-512, 2007; Bonaventure et al., FEBS J, 274: 3078-3093, 2007).

While long bone development involves endochondral ossification, craniofacial development is dependent on both endochondral and membranous ossification.

In skull vault, activated FGFR3 induces craniosiosynostosis. This disease consists of premature fusion of one or more of the cranial sutures. Two FGFR3 mutations cause specific craniosynostoses, Muenke syndrome and Crouzon syndrome with acanthosis *nigricans*. These diseases are an autosomal dominant hereditary disorder.

In long bone, FGFR3, when activated, exerts a negative regulatory influence mainly in the growth phase, in which it reduces the turnover necessary for bone elongation, the rate of cartilage template formation and disrupts chondrocyte proliferation and differentiation.

Abnormal FGFR3 overactivation or constitutive activation of FGFR3 leads to a severe disorganization of the growth plate cartilage. Gain of function mutants of FGFR3 (also called "constitutively active mutants of FGFR3") disrupt endochondral ossification in a spectrum of skeletal dysplasias which include achondroplasia (ACH), the most common form of human dwarfism, hypochondroplasia (HCH), and thanatophoric dysplasia (TD), the most common form of lethal skeletal dysplasia. On the contrary, it has been shown that FGFR3 knock-out mice and humans without functional FGFR3 demonstrate skeletal overgrowth.

Therefore, FGFR3-related skeletal diseases (e.g. FGFR3-related skeletal dysplasias and FGFR3-related craniosiosynostosis) are the result of increased signal transduction from the activated receptor.

Among skeletal dysplasias, achondroplasia is of particular interest since it is one of the most common congenital diseases responsible for dwarfism, disorder characterized by short limbs relative to trunk. It is diagnosed by growth failure in the major axes of the long bones of extremities and typical physical features such as a large frontally projecting cranium and a short nose. This disease is an autosomal dominant hereditary disorder, but most of cases are found to be sporadic. Hypochondroplasia is also characterized by short stature with disproportionately short arms and legs. The skeletal features are very similar to achondroplasia but usually tend to be milder.

Current therapies of achondroplasia and hypochondroplasia include orthopedic surgeries such as leg lengthening and growth hormone therapy. However, leg lengthening inflicts a great pain on patients, and growth hormone therapy increases body height by means of periodic growth hormone injections starting from childhood. Further, growth ceases when injections are stopped.

Consequently, it is desirable to develop a new achondroplasia and hypochondroplasia therapy and to identify molecules suitable for treating achondroplasia and hypochondroplasia, as well as other FGFR3-related skeletal diseases such as FGFR3-related craniosiosynostosis.

DESCRIPTION OF THE INVENTION

In an attempt to find a new treatment for skeletal diseases, the inventors succeeded in restoring bone growth by administering tyrosine kinase inhibitors, more particularly inhibitors which are able to inhibit auto-phosphorylation of FGFR3. Indeed, the inventors have shown in an ex vivo model (consisting of culturing femurs of embryonic dwarf mice which displays impaired endochondral ossification) that tyrosine kinase inhibitors (in particular those which prevent ATP from binding to the "ATP binding site" of FGFR3) restore a normal growth of the bones. Further, the inventors have shown in vivo in an animal model that administration of tyrosine kinase inhibitors (e.g. compounds that belong to the pyrido[2,3-d]pyrimidine class and to the N-aryl-N'-pyrimidin-4-yl urea class) improves dwarfism condition by increasing growth of bones.

Consequently, inhibitors of FGFR3 are useful for treating FGFR3-related skeletal diseases.

Therefore, the present invention provides a method for treating or preventing FGFR3-related skeletal diseases which comprises the step of administering at least one antagonist of the FGFR3 tyrosine kinase receptor, or a composition comprising such an antagonist, to a subject in need thereof.

The invention also relates to an antagonist of the FGFR3, or a composition comprising such an antagonist, for use in the treatment or prevention of FGFR3-related skeletal diseases.

As used herein, the terms "FGFR3", "FGFR3 tyrosine kinase receptor" and "FGFR3 receptor" are used interchangeably throughout the specification and refer to all of the naturally-occurring isoforms of FGFR3.

In particular, an antagonist of a FGFR3 tyrosine kinase receptor refers to an antagonist capable of inhibiting or blocking the activity of:
  a) a FGFR3 polypeptide comprising or consisting of the amino acid sequence shown in NCBI reference Np_000133 and in UniProt reference P22607 (sequence SEQ ID NO: 1); and/or
  b) a FGFR3 corresponding to the mature isoform of the a FGFR3 polypeptide of (a) (i.e. obtained after cleavage of the signal peptide); and/or
  c) an allelic variant of a FGFR3 of (a) or (b); and/or
  d) a splice variant of a FGFR3 of (a), (b) or (c); and/or
  e) a constitutively active mutant of a FGFR3 of (a), (b), (c) or (d).
  f) an isoform obtained by proteolytic processing of a FGFR3 of (a), (b), (c), (d) or (e).

As used herein, the expressions "constitutively active FGFR3 receptor variant", "constitutively active mutant of the FGFR3" or "mutant FGFR3 displaying a constitutive activity" are used interchangeably and refer to a mutant of said receptor exhibiting a biological activity (i.e. triggering downstream signaling) in the absence of FGF ligand stimulation, and/or exhibiting a biological activity which is higher than the biological activity of the corresponding wild-type receptor in the presence of FGF ligand.

A constitutively active FGFR3 variant according to the invention is in particular chosen from the group consisting of (residues are numbered according to their position in the precursor of fibroblast growth factor receptor 3 isoform 1-806 amino acids long-):
  a mutant wherein the serine residue at position 84 is substituted with lysine (named herein below S84L);
  a mutant wherein the arginine residue at position 248 is substituted with cysteine (named herein below R200C);
  a mutant wherein the arginine residue at position 248 is substituted with cysteine (named herein below R248C);
  a mutant wherein the serine residue at position 249 is substituted with cysteine (named herein below S249C);
  a mutant wherein the proline residue at position 250 is substituted with arginine (named herein below P250R);
  a mutant wherein the asparagine residue at position 262 is substituted with histidine (named herein below N262H);
  a mutant wherein the glycine residue at position 268 is substituted with cysteine (named herein below G268C);
  a mutant wherein the tyrosine residue at position 278 is substituted with cysteine (named herein below Y278C)
  a mutant wherein the serine residue at position 279 is substituted with cysteine (named herein below S279C);
  a mutant wherein the glycine residue at position 370 is substituted with cysteine (named herein below G370C);
  a mutant wherein the serine residue at position 371 is substituted with cysteine (named herein below S371C);
  a mutant wherein the tyrosine residue at position 373 is substituted with cysteine (named herein below Y373C);
  a mutant wherein the glycine residue at position 380 is substituted with arginine (named herein below G380R);
  a mutant wherein the valine residue at position 381 is substituted with glutamate (named herein below V381E);
  a mutant wherein the alanine residue at position 391 is substituted with glutamate (named herein below A391E);
  a mutant wherein the asparagine residue at position 540 is substituted with Lysine (named herein below N540K);
  a mutant wherein the termination codon is eliminated due to base substitutions, in particular the mutant wherein the termination codon is mutated in an arginine, cysteine, glycine, serine or tryptophane codon (named herein below X807R, X807C, X807G, X807S and X807W, respectively);
  a mutant wherein the lysine residue at position 650 is substituted with another residue, in particular with methionine, glutamate, asparagine or glutamine (named herein below K650M, K650E, K650N and K6500).

Preferably, a constitutively active FGFR3 variant according to the invention is K650M, K650E or Y373C mutant.

In the context of the present invention, the term "FGFR3-related skeletal disease" is intended to mean a skeletal disease that is caused by an abnormal increased activation of FGFR3, in particular by expression of a constitutively active mutant of the FGFR3 receptor, in particular a constitutively active mutant of the FGFR3 receptor as described above.

The FGFR3-related skeletal diseases are preferably FGFR3-related skeletal dysplasias and FGFR3-related craniosynostosis.

The FGFR3-related skeletal dysplasias according to the invention may correspond to an inherited or to a sporadic disease.

As used herein, the term "FGFR3-related skeletal dysplasias" includes but is not limited to thanatophoric dysplasia type I, thanatophoric dysplasia type II, hypochondroplasia, achondroplasia and SADDAN (severe achondroplasia with developmental delay and acanthosis *nigricans*).

In a preferred embodiment, the FGFR3-related skeletal dysplasia is caused by expression in the subject of a constitutively active FGFR3 receptor variant such as defined above.

In a preferred embodiment, the FGFR3-related skeletal dysplasia is a achondroplasia caused by expression of the G380R constitutively active mutant of the FGFR3 receptor.

In a preferred embodiment, the FGFR3-related skeletal dysplasia is a hypochondroplasia caused by expression of the N540K, K650N, K650Q, S84L, R200C, N262H, G268C, Y278C, S279C, V381E, constitutively active mutant of the FGFR3 receptor.

In a preferred embodiment, the FGFR3-related skeletal dysplasia is a thanatophoric dysplasia type I caused by expression of a constitutively active mutant of the FGFR3 receptor chosen from the group consisting of R248C, S248C, G370C, S371C; Y373C, X807R, X807C, X807G, X807S, X807W and K650M FGFR3 receptors.

In a preferred embodiment, the FGFR3-related skeletal dysplasia is a thanatophoric dysplasia type II caused by expression of the K650E constitutively active mutant of the FGFR3 receptor.

In a preferred embodiment, the FGFR3-related skeletal dysplasia is a severe severe achondroplasia with developmental delay and acanthosis *nigricans* caused by expression of the K650M constitutively active mutant of the FGFR3 receptor The FGFR3-related craniosynostosis according to the invention may correspond to an inherited or to a sporadic disease.

In a preferred embodiment, the FGFR3-related craniosynostosis is Muenke syndrome caused by expression of the P250R constitutively active mutant of the FGFR3 receptor or Crouzon syndrome with acanthosis *nigricans* caused by expression of the A391G constitutively active mutant of the FGFR3 receptor.

As used herein the term "antagonist" refers to an agent (i.e. a molecule) which inhibits or blocks the activity of FGFR3. For instance, an antagonist of FGFR3 refers to a molecule which inhibits or blocks the activity of the FGFR3 receptor. Preferably, the FGFR3 antagonists according to the invention act through direct interaction with the FGFR3 receptor.

The antagonists of the present invention act by blocking or reducing FGFR3 receptor functional activation. This may for example be achieved by interfering with FGF ligand binding to FGFR3 receptor or with ATP binding to "ATP binding site" of FGFR3 receptor for preventing phosphorylation of tyrosine residues located towards the cytoplasmic domain (activation loop), i.e. on $Tyr^{648}$ and $Tyr^{647}$.

Alternatively, this may be achieved by reducing or preventing expression of FGFR3 receptor.

The term "expression" when used in the context of expression of a gene or nucleic acid refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein (i.e. FGFR3) produced by translation of a mRNA.

Both options ultimately result in blocking or reducing signal transduction, hence in blocking or reducing receptors functional activity.

The antagonists according to the invention are capable of inhibiting or eliminating the functional activation of the FGFR3 receptor in viva and/or in vitro. The antagonist may inhibit the functional activation of the FGFR3 receptor by at least about 10%, preferably by at least about 30%, preferably by at least about 50%, preferably by at least about 70, 75 or 80%, still preferably by 85, 90, 95, or 100%.

Preferably, the antagonists according to the invention are more specific for FGFR3 versus FGFR1, 2 and 4, for instance the inhibitor constant "KI" of the antagonists for FGFR3 is at least 2, preferably 5, more preferably 10, times lower than the KI for at least one of FGFR1, 2 and 4.

Antagonists for FGFR3 receptor are well-known to those skilled in the art and include, e.g., anti-FGFR3 antibodies, for instance the antibodies described by Rauchenberger, R. et al. (J. Biol. Chem. 2003 Oct. 3; 278(40):38194-205.), Martinez-Torrecuadrada, J., et al. (Clin. Cancer Res. 2005 Sep. 1; 11(17):6280-90), Trudel S., et al., (Blood 2006 May 15; 107(10):4039-46.), Qing J. et al. (J. Clin. Invest. 2009, 119(5):1216-29), the anti-FGFR3 antibodies disclosed in IN2011CN02023, WO2010/111367, US 2010/0098696, WO2010/02862, WO2007/144893, WO2002/102973.

Antagonists for FGFR3 receptor also include small chemical molecules, for instance those disclosed in WO2010/22169 (e.g. the compound of general formula 1 corresponding to 4,4',4",4"'-[carbonyl-bis[imino-5,1,3-benzenetriyl bis-{carbonylimino}]3tetrakis-{benzene-1,3-disulfonic acid}), WO2007/26251, WO2005/47244, US2005/261307, as well as nucleic acid compounds for regulating/inhibiting FGFR3 expression described in WO2003/23004, US2007/049545 and WO2011/139843.

Functional activation of the FGFR3 receptor may be readily assessed by the one skilled in the art according to known methods. Indeed, since activated FGFR3 receptor is phosphorylated on tyrosine residues located towards the cytoplasmic domain, i.e. on $Tyr^{48}$ and $Tyr^{47}$, functional activation of the FGFR3 receptor may for example be assessed by measuring its phosphorylation.

For instance, analysis of ligand-induced phosphorylation of the FGFR3 receptor can be preformed as described in Le Corre et al. (Org. Biomol. Chem., 8: 2164-2173, 2010).

Alternatively, receptor phosphorylation in cells can be readily detected by immunocytochemistry, immunohistochemistry and/or flow cytometry using antibodies which specifically recognize this modification. For instance phosphorylation of FGFR3 on the $Tyr^{648}$ and $Tyr^{647}$ residues can be detected by immunocytochemistry, immunohistochemistry and/or flow cytometry using monoclonal or polyclonal antibodies directed against phosphorylated $Tyr^{648}$ and $Tyr^{647}$-FGFR3.

Functional activation of the FGFR3 receptor may also be tested by using FGFR3-dependent cell lines (for instance BaF3 cell line). The FGFR3 antagonist activity of a compound is determined by measuring its ability to inhibit the proliferation of a FGFR3-dependent cell line (see methods described by Vito Guagnano et al., Journal of Medicinal Chemistry, 54: 7066-7083, 2011).

Further, FGFR3, when associated with its ligand, mediates signaling by activating the ERK and p38 MAP kinase pathways, and the STAT pathway. Therefore activation of FGFR3 receptor can also be assessed by determining the activation of these specific pathways as described by Horton et al. (lancet, 370: 162-172, 2007)

Accordingly, an antagonist may be identified as a molecule which reduces the level of phosphorylation of the receptor to be tested upon stimulation with its specific ligand of a cell expressing said receptor, as compared with the level of receptor phosphorylation measured in the cell when stimulated with its specific ligand in the absence of the antagonist.

The antagonists according to the present invention include those which specifically bind to the FGFR3 receptor, thereby reducing or blocking signal transduction. Antagonists of this type include antibodies (in particular the antibodies as disclosed above) or aptamers which bind to FGFR3, fusion polypeptides, peptides, small chemical molecules which bind to FGFR3, and peptidomimetics.

The term "small chemical molecule" refers to a molecule, preferably of less than 1,000 daltons, in particular organic or inorganic compounds. Structural design in chemistry should help to find such a molecule.

According to a preferred embodiment, the small chemical molecule prevents binding of ATP to the "ATP binding site" of FGFR3. In a more preferred embodiment, the small chemical molecule which prevents binding of ATP to the "ATP binding site" of FGFR3 belongs to the pyrido[2,3-d] pyrimidine class.

More preferably, the small chemical molecule which prevents binding of ATP to the "ATP binding site" of FGFR3 is selected from the group consisting of the compounds PD173074, 18, 19a to 19 m, 22b, 22c, 23b to 23f disclosed in table below (as well as in FIG. 2*a* and Scheme 3 of the article by Le Corre et al., Org. Biomol. Chem., 8: 2164-2173, 2010).

| Composé | Structure |
|---|---|
| PD173074 | 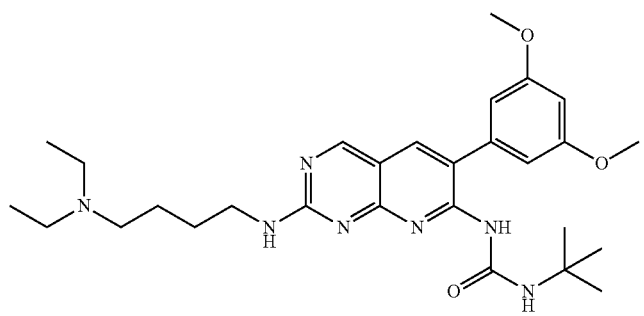 [SMILES: CCN(CC)CCCCNc1ncc2cc(-c3cc(OC)cc(OC)c3)c(NC(=O)NC(C)(C)C)nc2n1] |
| 19a | 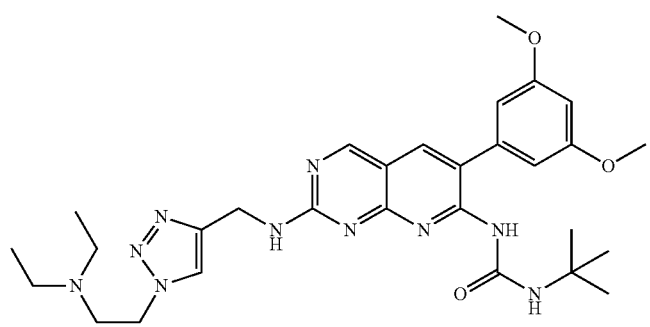 [SMILES: CCN(CC)CCn1cc(CNc2ncc3cc(-c4cc(OC)cc(OC)c4)c(NC(=O)NC(C)(C)C)nc3n2)nn1] |
| 19b | 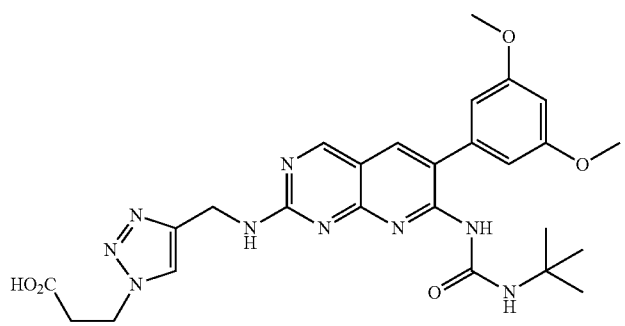 [SMILES: COc1cc(OC)cc(-c2cc3cnc(NCc4cn(CCC(=O)O)nn4)nc3nc2NC(=O)NC(C)(C)C)c1] |
| 19c | 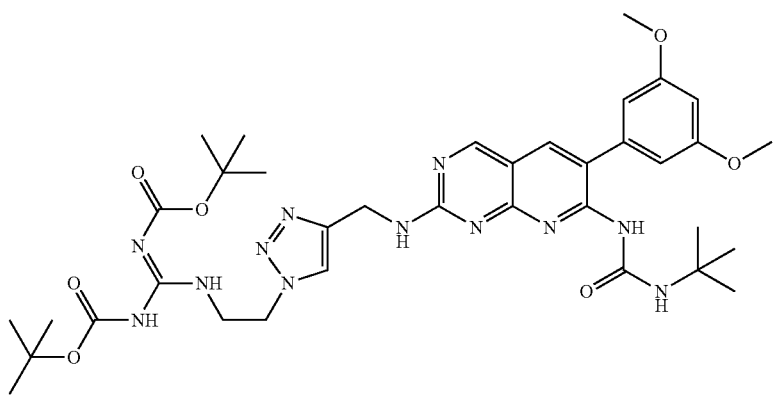 [SMILES: COc1cc(OC)cc(-c2cc3cnc(NCc4cn(CCN/C(=N\C(=O)OC(C)(C)C)NC(=O)OC(C)(C)C)nn4)nc3nc2NC(=O)NC(C)(C)C)c1] |

-continued
| Composé | Structure |
|---|---|
| 19d | 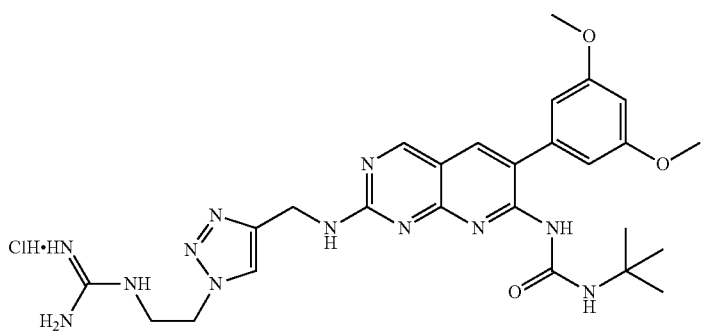 |
| 19e | 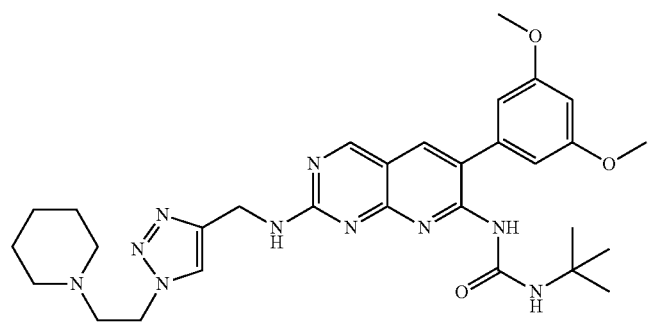 [SMILES: COc1cc(OC)cc(-c2cc3cnc(NCc4cn(CCN5CCCCC5)nn4)nc3nc2NC(=O)NC(C)(C)C)c1] |
| 19f | 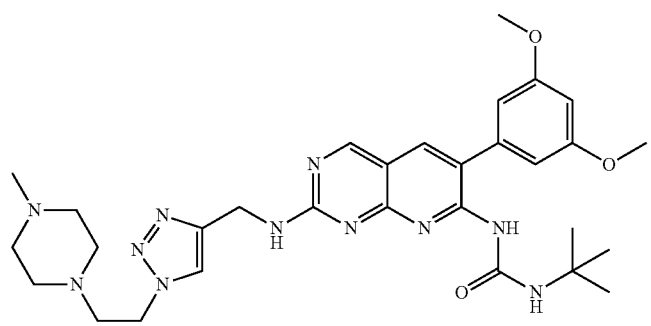 [SMILES: COc1cc(OC)cc(-c2cc3cnc(NCc4cn(CCN5CCN(C)CC5)nn4)nc3nc2NC(=O)NC(C)(C)C)c1] |
| 19g | 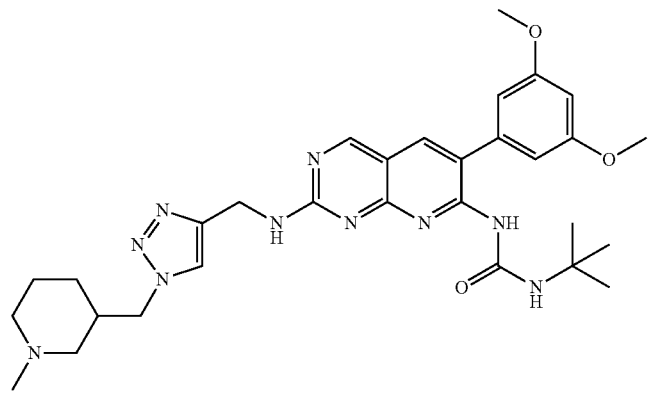 [SMILES: COc1cc(OC)cc(-c2cc3cnc(NCc4cn(CC5CCCN(C)C5)nn4)nc3nc2NC(=O)NC(C)(C)C)c1] |

-continued
| Composé | Structure |
|---|---|
| 19h | 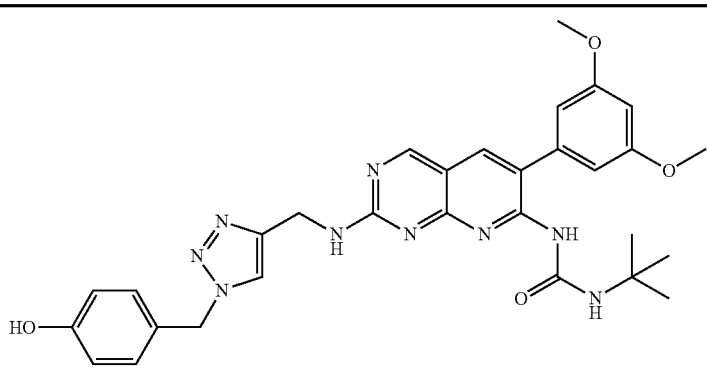 |
| 19i | 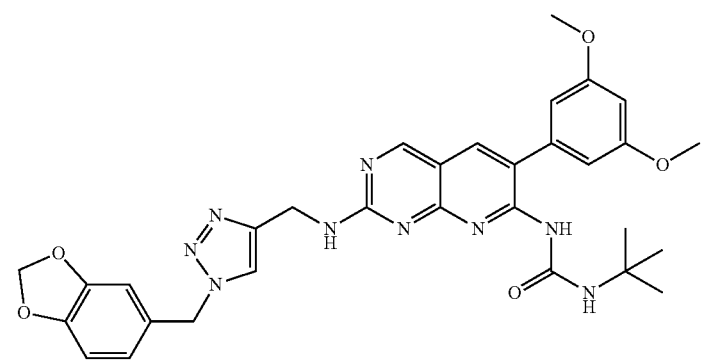 [SMILES: COc1cc(OC)cc(-c2cc3cnc(NCc4cn(Cc5ccc6c(c5)OCO6)nn4)nc3nc2NC(=O)NC(C)(C)C)c1] |
| 19j | 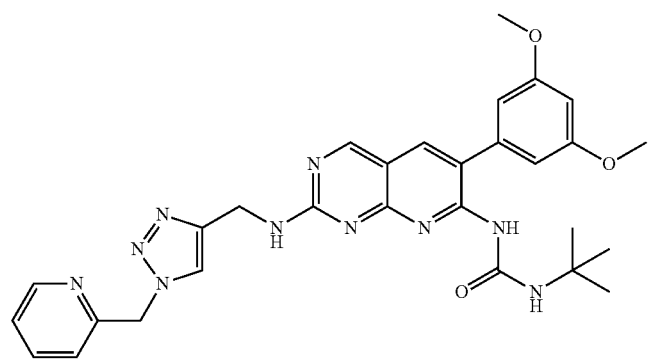 [SMILES: COc1cc(OC)cc(-c2cc3cnc(NCc4cn(Cc5ccccn5)nn4)nc3nc2NC(=O)NC(C)(C)C)c1] |
| 19k | 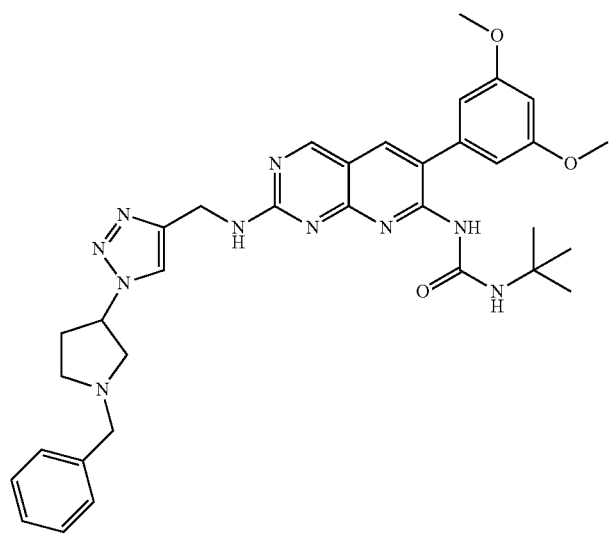 [SMILES: COc1cc(OC)cc(-c2cc3cnc(NCc4cn(C5CCN(Cc6ccccc6)C5)nn4)nc3nc2NC(=O)NC(C)(C)C)c1] |

| Composé | Structure |
|---|---|
| 19l | 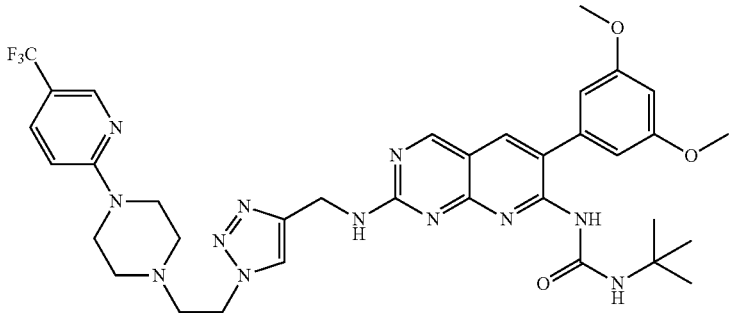 [SMILES: COc1cc(OC)cc(-c2cc3cnc(NCc4cn(CCN5CCN(c6ccc(C(F)(F)F)cn6)CC5)nn4)nc3nc2NC(=O)NC(C)(C)C)c1] |
| 19m | 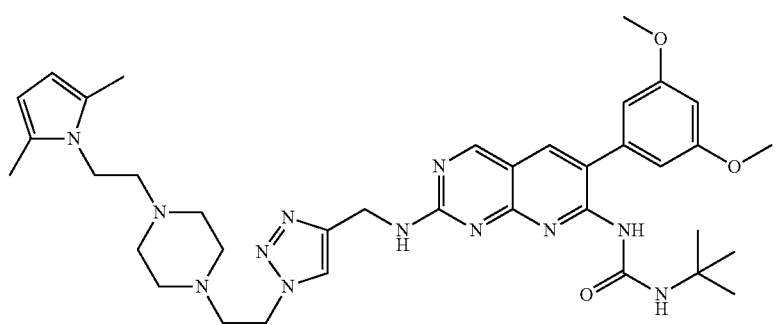 |
| 22b | 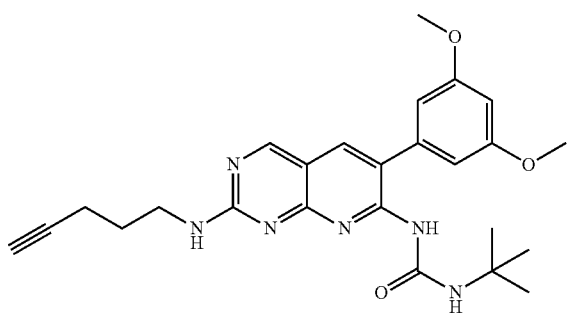 [SMILES: C#CCCCNc1ncc2cc(-c3cc(OC)cc(OC)c3)c(NC(=O)NC(C)(C)C)nc2n1] |
| 22c | 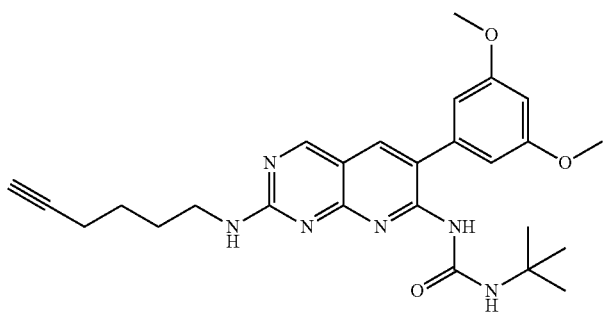 [SMILES: C#CCCCCNc1ncc2cc(-c3cc(OC)cc(OC)c3)c(NC(=O)NC(C)(C)C)nc2n1] |

-continued
| Composé | Structure |
|---|---|
| 23b | 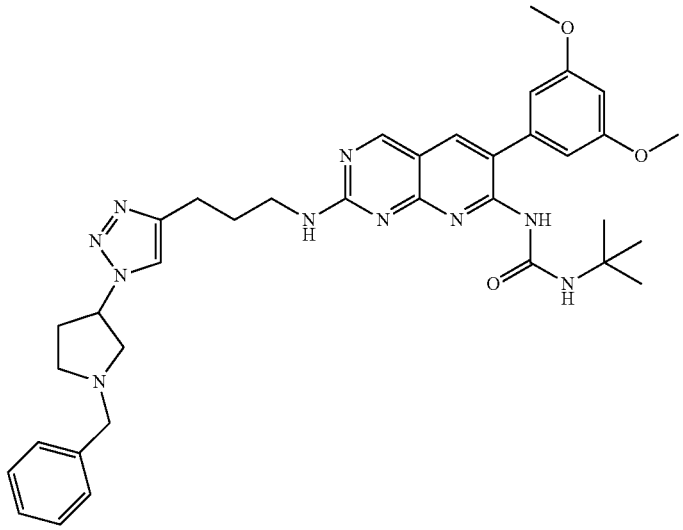 [SMILES: COc1cc(OC)cc(-c2cc3cnc(NCCCc4cn(C5CCN(Cc6ccccc6)C5)nn4)nc3nc2NC(=O)NC(C)(C)C)c1] |
| 23c | 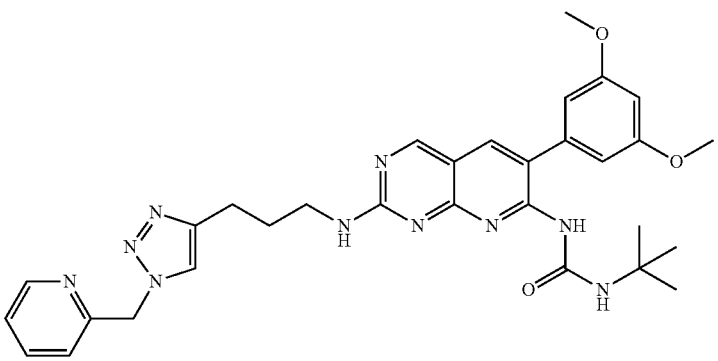 [SMILES: COc1cc(OC)cc(-c2cc3cnc(NCCCc4cn(Cc5ccccn5)nn4)nc3nc2NC(=O)NC(C)(C)C)c1] |
| 23d | 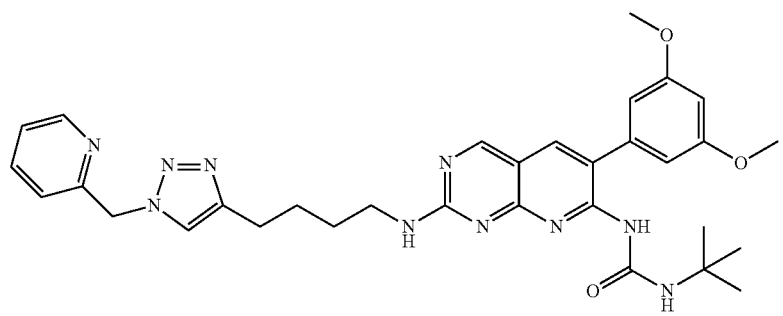 [SMILES: COc1cc(OC)cc(-c2cc3cnc(NCCCCc4cn(Cc5ccccn5)nn4)nc3nc2NC(=O)NC(C)(C)C)c1] |
| 23e | 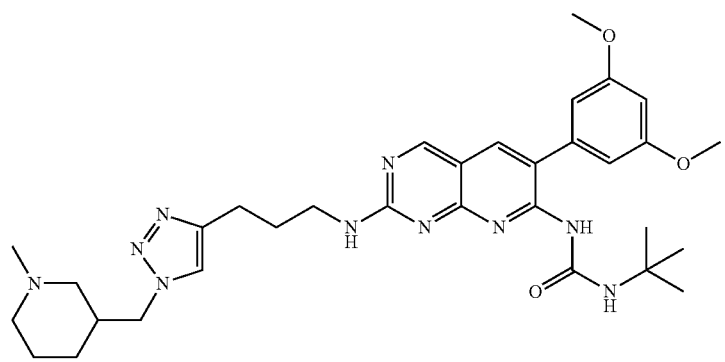 [SMILES: COc1cc(OC)cc(-c2cc3cnc(NCCCc4cn(CC5CCCN(C)C5)nn4)nc3nc2NC(=O)NC(C)(C)C)c1] |

| Composé | Structure |
|---|---|
| 23f | 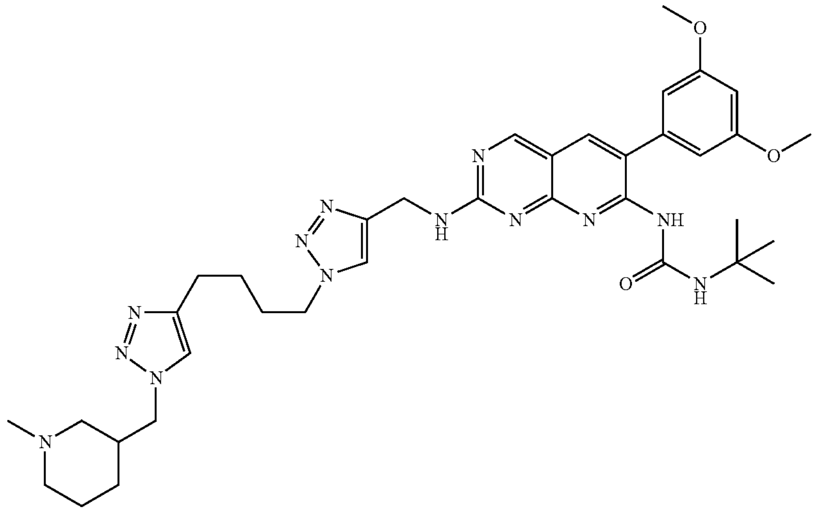 |

Advantageously, the small chemical molecule which prevents binding of ATP to the "ATP binding site" of FGFR3 is the compound PD173075 or the compound 19g, corresponding to compound "A31" disclosed in FIG. 1A of the present application and in Table A.

In another more preferred embodiment, the small chemical molecule which prevents binding of ATP to the "ATP binding site" of FGFR3 belongs to the N-aryl-N'-pyrimidin-4-yl urea class.

More preferably, the small chemical molecule which prevents binding of ATP to the "ATP binding site" of FGFR3 is selected from the group consisting of the compounds 1a to 1n disclosed in Table B below (as well as in Table 1 of the article by Vito Guagnano et al., Journal of Medicinal Chemistry, 54: 7066-7083, 2011).

Advantageously, the small chemical molecule which prevents binding of ATP to the "ATP binding site" of FGFR3 is the compound 1 h (also named BGJ-398), disclosed in the Table B below.

TABLE B

| Compound | Structure |
|---|---|
| 1a | 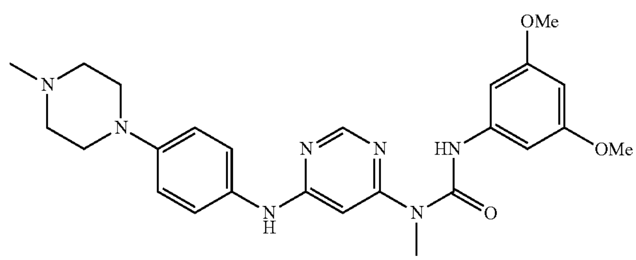 [SMILES: COc1cc(NC(=O)N(C)c2cc(Nc3ccc(N4CCN(C)CC4)cc3)ncn2)cc(OC)c1] |
| 1b | 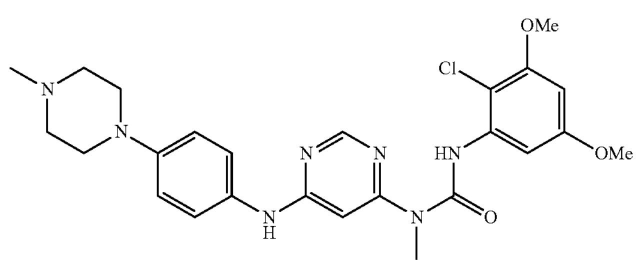 [SMILES: COc1cc(NC(=O)N(C)c2cc(Nc3ccc(N4CCN(C)CC4)cc3)ncn2)c(Cl)c(OC)c1] |

TABLE B-continued
| Compound | Structure |
| --- | --- |
| 1c | 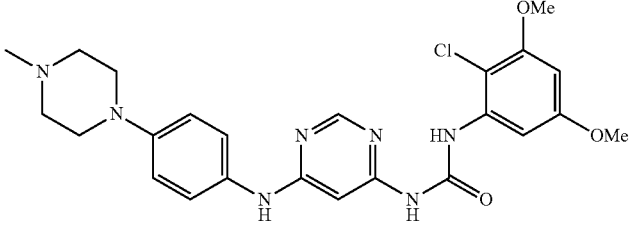 [SMILES: COc1cc(NC(=O)Nc2cc(Nc3ccc(N4CCN(C)CC4)cc3)ncn2)c(Cl)c(OC)c1] |
| 1d | 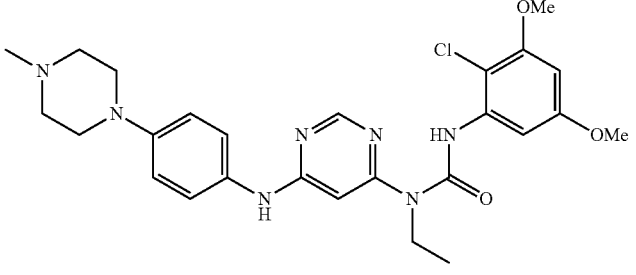 [SMILES: CCN(C(=O)Nc1cc(OC)cc(OC)c1Cl)c1cc(Nc2ccc(N3CCN(C)CC3)cc2)ncn1] |
| 1e | 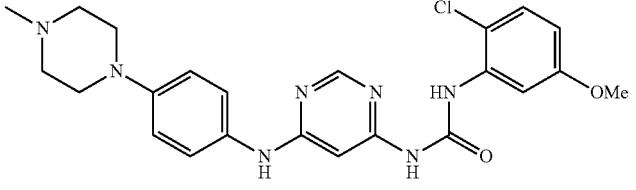 [SMILES: COc1ccc(Cl)c(NC(=O)Nc2cc(Nc3ccc(N4CCN(C)CC4)cc3)ncn2)c1] |
| 1f | 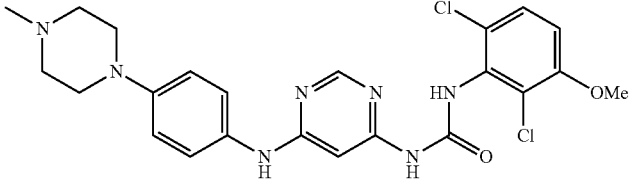 [SMILES: COc1ccc(Cl)c(NC(=O)Nc2cc(Nc3ccc(N4CCN(C)CC4)cc3)ncn2)c1Cl] |
| 1g | 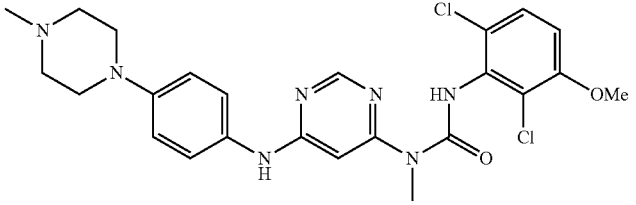 [SMILES: COc1ccc(Cl)c(NC(=O)N(C)c2cc(Nc3ccc(N4CCN(C)CC4)cc3)ncn2)c1Cl] |

TABLE B-continued

| Compound | Structure |
| --- | --- |
| 1h | 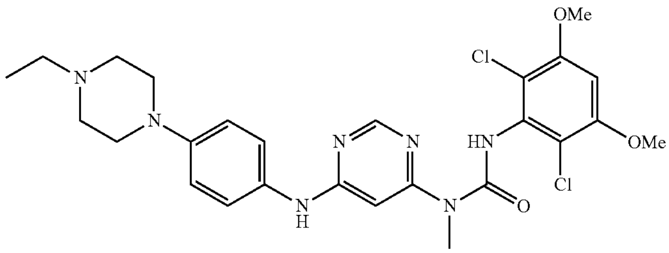 [SMILES: CCN1CCN(c2ccc(Nc3cc(N(C)C(=O)Nc4c(Cl)c(OC)cc(OC)c4Cl)ncn3)cc2)CC1] |
| 1i | 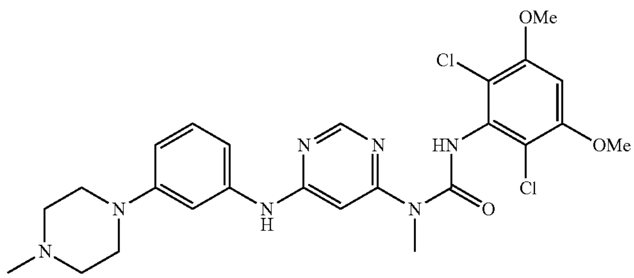 [SMILES: COc1cc(OC)c(Cl)c(NC(=O)N(C)c2cc(Nc3cccc(N4CCN(C)CC4)c3)ncn2)c1Cl] |
| 1j | 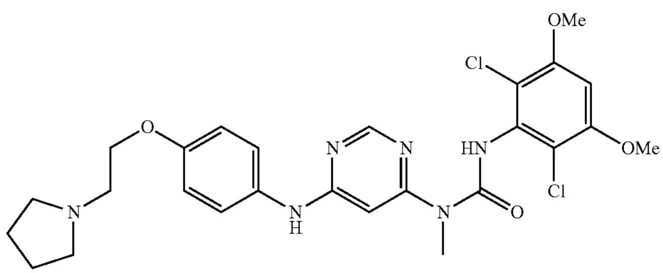 [SMILES: COc1cc(OC)c(Cl)c(NC(=O)N(C)c2cc(Nc3ccc(OCCN4CCCC4)cc3)ncn2)c1Cl] |
| 1k | 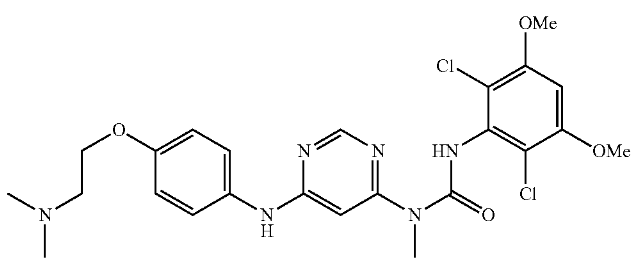 [SMILES: COc1cc(OC)c(Cl)c(NC(=O)N(C)c2cc(Nc3ccc(OCCN(C)C)cc3)ncn2)c1Cl] |
| 1l | 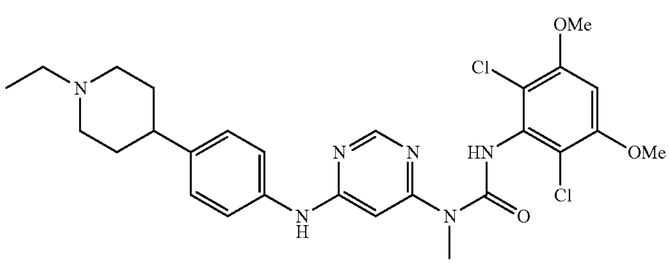 [SMILES: CCN1CCC(c2ccc(Nc3cc(N(C)C(=O)Nc4c(Cl)c(OC)cc(OC)c4Cl)ncn3)cc2)CC1] |

TABLE B-continued

| Compound | Structure |
|---|---|
| 1m | *(structure: 4-methylpiperazinylmethyl-phenyl-amino-pyrimidine linked via N-methyl urea to 2,6-dichloro-3,5-dimethoxyphenyl)* |
| 1n | *(structure: dimethylaminomethyl-phenyl-amino-pyrimidine linked via N-methyl urea to 2,6-dichloro-3,5-dimethoxyphenyl)* |

As used herein the term "polypeptide" refers to any chain of amino acids linked by peptide bonds, regardless of length or post-translational modification. Polypeptides include natural proteins, synthetic or recombinant polypeptides and peptides (i.e. polypeptides of less than 50 amino acids) as well as hybrid, post-translationally modified polypeptides, and peptidomimetic.

As used herein, the term "amino acid" refers to the 20 standard alpha-amino acids as well as naturally occurring and synthetic derivatives. A polypeptide may contain L or D amino acids or a combination thereof.

As used herein the term "peptidomimetic" refers to peptide-like structures which have non-amino acid structures substituted but which mimic the chemical structure of a peptide.

The term "antibody" refers to immunoglobulin molecules and immunologically active portions of immunoglobulin molecules, i.e., molecules that contain an antigen binding site that immunospecifically binds an antigen. As such, the term antibody encompasses not only whole antibody molecules, but also antibody fragments as well as variants (including derivatives) of antibodies and antibody fragments.

In particular, the antibody according to the invention may correspond to a polyclonal antibody, a monoclonal antibody (e.g. a chimeric, humanized or human antibody), a fragment of a polyclonal or monoclonal antibody or a diabody.

"Antibody fragments" comprise a portion of an intact antibody, preferably the antigen binding or variable region of the intact antibody. Examples of antibody fragments include Fv, Fab, F(ab)$_2$, Fab', Fd, dAb, dsFv, scFv, sc(Fv)$_2$, CDRs, diabodies and multi-specific antibodies formed from antibodies fragments.

Antibodies according to the invention may be produced by any technique known in the art, such as, without limitation, any chemical, biological, genetic or enzymatic technique, either alone or in combination. The antibodies of this invention can be obtained by producing and culturing hybridomas.

According to a preferred embodiment, the antagonist is an antibody which specifically recognizes and binds to the FGFR3 receptor and prevents binding of ATP to the ATP binding site of FGFR3.

In another embodiment, the antagonist is an antibody which prevents functional oligomerization of the receptor.

"Aptamers" are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., Science, 1990, 249(4968):505-10. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., Clin. Chem., 1999, 45(9): 1628-50. Peptide aptamers consists of a conformationally constrained antibody variable region displayed by a platform protein, such as *E. coli* Thioredoxin A that are selected from combinatorial libraries by two hybrid methods (Colas et al., Nature, 1996, 380, 548-50).

In order to target the antagonist of the invention specifically to growth plate chondrocytes, the antagonist may be tagged with molecules that possess affinity for cartilage or chondrocytes. Such molecules are for instance described by Rothenfluh et al. (Nat Mater 7: 248-254, 2008), and Laroui H et al. (Biomacromolecules, 8: 1041-1021, 2007).

The antagonist of the invention can be used in combination with growth hormones and/or substances activating guanylyl cyclase B (such as the substances disclosed in application US 2003/0068313).

The antagonists comprises in the combination are intended to be administered simultaneously or sequentially.

Thus, the present invention also relates to a combination of at least one antagonist of the invention and at least one other agent such as growth hormones and/or substances activating guanylyl cyclase B, for sequential or simultaneous use in the treatment or prevention of a FGFR3-related skeletal dysplasia.

The antagonist or combination used in the above recited method or use are provided in a pharmaceutically acceptable carrier, excipient or diluent which is not prejudicial to the patient to be treated.

Pharmaceutically acceptable carriers and excipient that may be used in the compositions of this invention include, but are not limited to, ion exchangers, alumina, aluminium stearate, lecithin, self-emulsifying drug delivery systems (SEDDS) such as d-a-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

As appreciated by skilled artisans, compositions are suitably formulated to be compatible with the intended route of administration. Examples of suitable routes of administration include parenteral route, including for instance intramuscular, subcutaneous, intravenous, intraperitoneal or local intratumoral injections. The oral route can also be used, provided that the composition is in a form suitable for oral administration, able to protect the active principle from the gastric and intestinal enzymes.

Further, the amount of antagonist or combination used in the above recited method or use is a therapeutically effective amount. A therapeutically effective amount of antagonist is that amount sufficient to achieve growth of bones or cartilages, or to treat a desired disease without causing overly negative effects in the subject to which the antagonist or the combination is administered. The exact amount of antagonist to be used and the composition to be administered will vary according to the age and the weight of the patient being treated, the type of disease, the mode of administration, the frequency of administration as well as the other ingredients in the composition which comprises the antagonist. Generally, the antagonist for use in the treatment or prevention of FGFR3-related skeletal dysplasias may be administered in the rage from about 100 µg/kg to 1 mg/kg, alternatively from about 1 mg to about 10 mg/Kg, alternatively from about 10 mg to about 100 mg/Kg. Effective doses will also vary depending on route of administration, as well as the possibility of co-usage with other agents.

When the antagonist belongs to the pyrido[2,3-d]pyrimidine class, it is preferably administered in the range from about 1 mg/kg to about 10 mg/Kg. Typically, antagonist PD173074 is administered from about 1 mg/kg to about 10 mg/Kg, preferably from 2 mg/kg to about 8 mg/Kg, more preferably 4 mg/kg to about 6 mg/Kg. When the antagonist belongs to the N-aryl-N'-pyrimidin-4-yl urea class, it is preferably administered in the range from about 1 mg/kg to about 10 mg/Kg. Typically, antagonist BGJ-398 is administered from about 1 mg/kg to about 10 mg/Kg, preferably from 2 mg/kg to about 8 mg/Kg, more preferably 4 mg/kg to about 6 mg/Kg. Advantageously, BGJ-398 is administered to 1.66 mg/kg.

As used herein, the term "subject" denotes a human or non-human mammal, such as a rodent, a feline, a canine, or a primate. Preferably, the subject is a human being, more preferably a child (i.e. a child who is growing up). Preferably, when the subject to be treated is a child, the antagonist is administered during all or part of child growth period.

In the context of all the invention, the term "treating" is used herein to characterize a therapeutic method or process that is aimed at (1) slowing down or stopping the progression, aggravation, or deterioration of the symptoms of the disease state or condition to which such term applies; (2) alleviating or bringing about ameliorations of the symptoms of the disease state or condition to which such term applies; and/or (3) reversing or curing the disease state or condition to which such term applies.

As used herein, the term "preventing" intends characterizing a prophylactic method or process that is aimed at delaying or preventing the onset of a disorder or condition to which such term applies.

Throughout the present application, the references to entries of public databases refer to the entries in force on Nov. 23, 2011. Further, throughout this application, various references are cited. The disclosures of these references are hereby incorporated by reference into the present disclosure.

The present invention will be further illustrated by the additional description which follows, which refer to examples which show that administration tyrosine kinase inhibitors, in particular a compound which belong to the pyrido[2,3-d]pyrimidine class or to the N-aryl-N'-pyrimidin-4-yl urea class, restores bone growth in ex vivo and in vivo models. It should be understood however that the invention is defined by the claims, and that these examples are given only by way of illustration of the invention and do not constitute in anyway a limitation thereof.

(A) Molecular scheme of the A31 compound. (B) Overall structure showing docking conformation of A31 inside the FGFR3 binding pocket. A31 is represented with rods. (C) Overall structure showing A31 in the ATP binding site.

Figure 2:
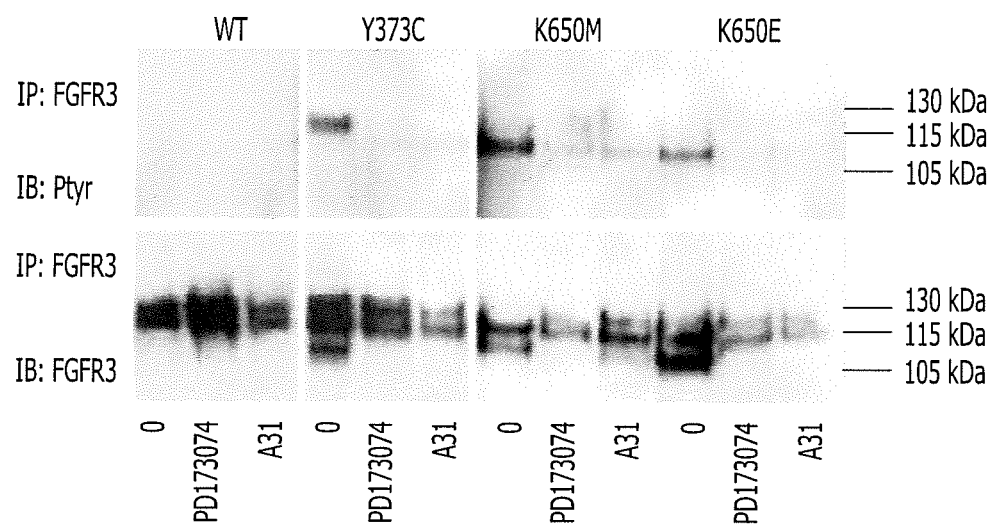

FIG. 2. A31 inhibits the constitutive activation of FGFR3.

Immunoblots showing FGFR3 overexpression in transfected cells (HEK) with WT human-cDNA (FGFR3$^{+/+}$) and 3 human mutant cDNA constructs (FGFR3$^{Y373C}$, FGFR3$^{K650E}$, FGFR3$^{K550M}$). FGFR3 is immunoprecipitated (IP) and immunoblotted (IB) with anti-FGFR3 and antiphosphotyrosine antibodies (Ptyr). Ptyr immunoblot showing constitutive phosphorylation of FGFR3 in transfected cells with mutant cDNA constructs. FGFR3 immunoblots showing three isoforms of the protein (105, 115 and 130 kDa) in WT (FGFR3$^{+/+}$) and one mutant (FGFR3$^{Y373C/+}$). Two isoforms of FGFR3 protein (105 kDa and 115 kDa) were present in cells transfected with mutant constructs (FGFR3$^{K650M}$ and FGFR3$^{K650E}$). A31 reduces the constitutive phosphorylation of FGFR3.

Figure 3:
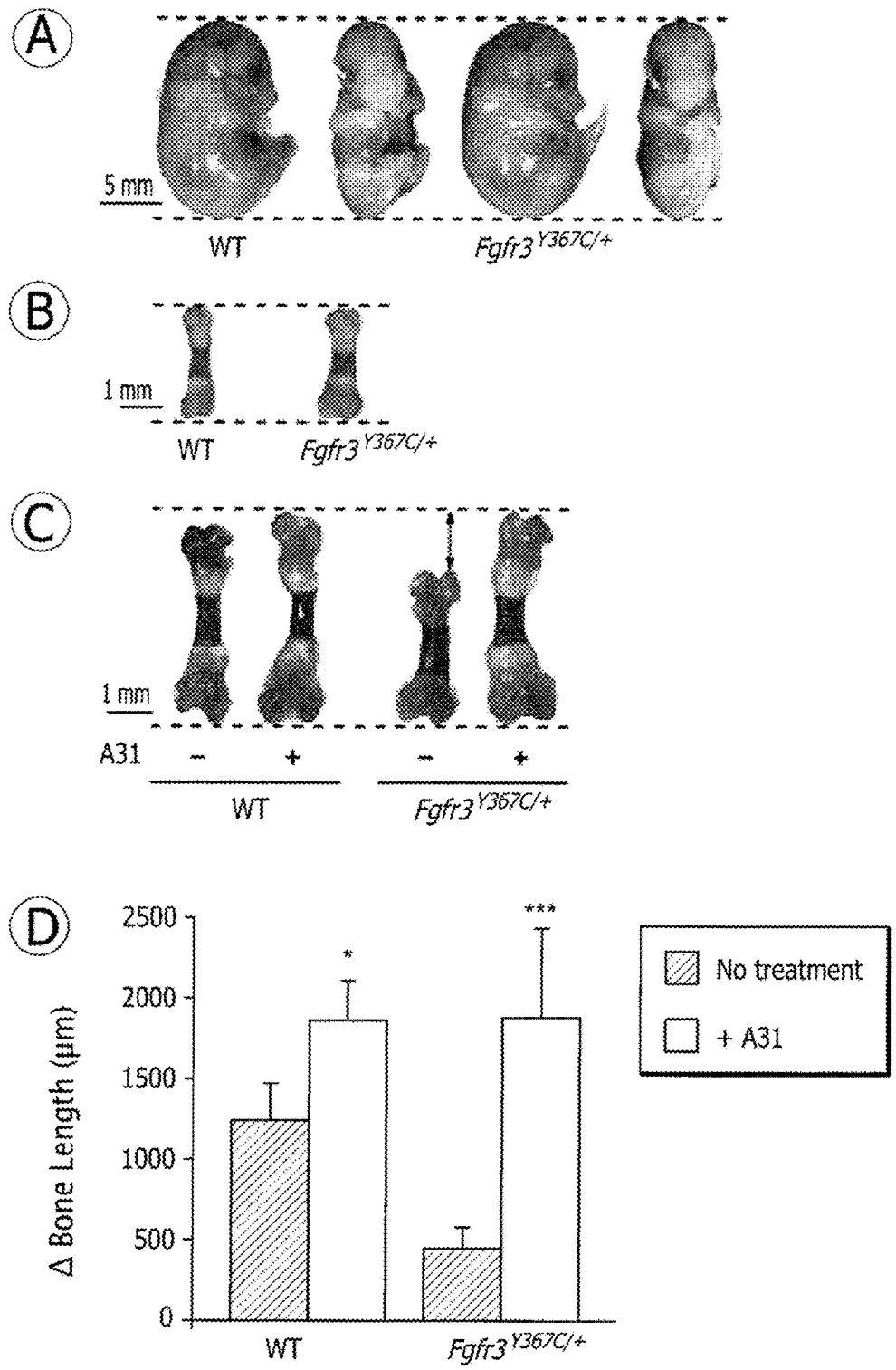

FIG. 3. A31 restores longitudinal bone growth of Fgfr3Y367C/+ femurs.

(A) Fgfr3$^{Y367C/+}$ mouse embryo at E16.5 shows a dome-shape skull. (B) Fgfr3$^{Y367C/+}$ femur is broader with a shorter diaphysis at E16.5 (C) Alizarin red and alcian blue staining show the small size of Fgfr3$^{Y357C/+}$ femurs. A31 increases the size of the Fgfr3$^{Y357C/+}$ femurs after 5 days of culture. (D) Bone length measurements showing a reduced longitudinal growth in Fgfr3$^{Y357C/+}$ femurs compared with WT (Fgfr3$^{Y367C/+}$, 461±119 µm; WT, 1247±227 µm; p<10$^{10}$). A31 enhances longitudinal growth in Fgfr3$^{Y357C/+}$ femurs, the bone growth is greater in Fgfr3$^{Y377C/+}$ femurs compared with controls (Fgfr3$^{Y367C/}$+, 1880±558 µm; WT, 1863±255 µm; ***p<10$^{-19}$ versus untreated controls). The experiments were performed 6 times and bone length is shown as mean+/−s.d.

Figure 4:
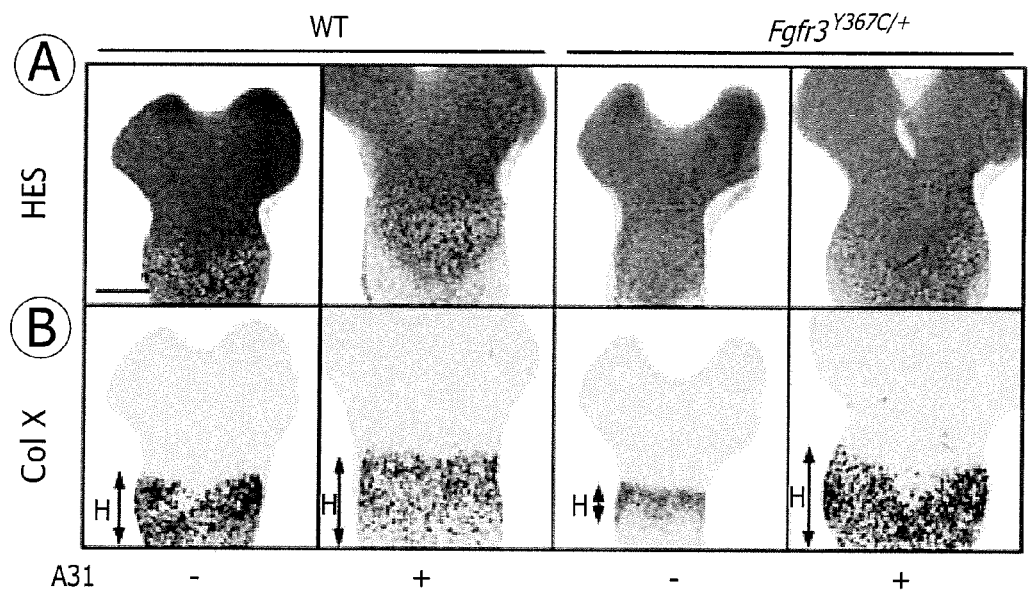

FIG. 4. A31 modifies the size of the growth plate and chondrocyte morphology.

(A) HES staining showing the reduced size of the Fgfr3$^{Y367C/+}$ growth plate. A31 induces an increase in the size of the growth plate of the Fgfr3$^{Y367C/+}$ mice. (B) In situ hybridization of type X collagen showing a markedly reduced hypertrophic zone (see the size of "H" symbolized by the size of the double-headed arrows) of Fgfr3$^{Y357C/+}$ growth plates compared with WT. A31 induces enhanced type X collagen expression in Fgfr3$^{Y367C/+}$ growth plates.

Figure 5:
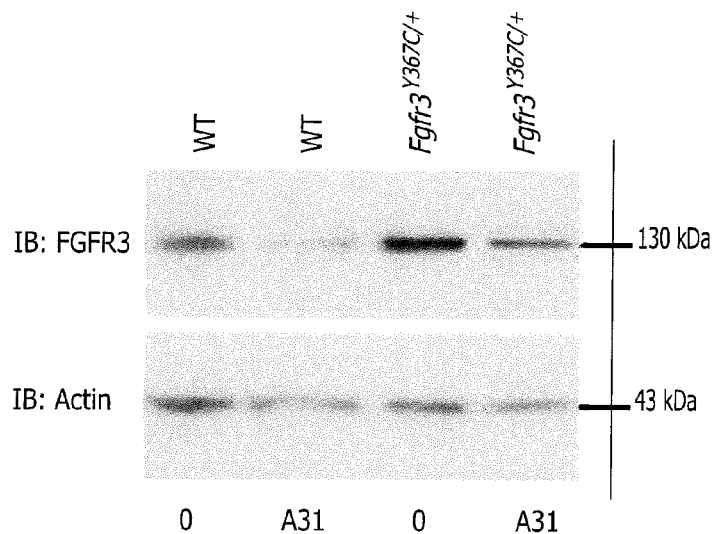

FIG. 5. A31 decreases Fgfr3 overexpression in Fgfr3Y367C/+ femurs.

Costal primary chondrocytes were examined by western-blot with anti-FGFR3. Fgfr3 protein level is higher in Fgfr3$^{Y367C/+}$ chondrocytes compared with WT. A31 reduced this overexpression.

Figure 6:
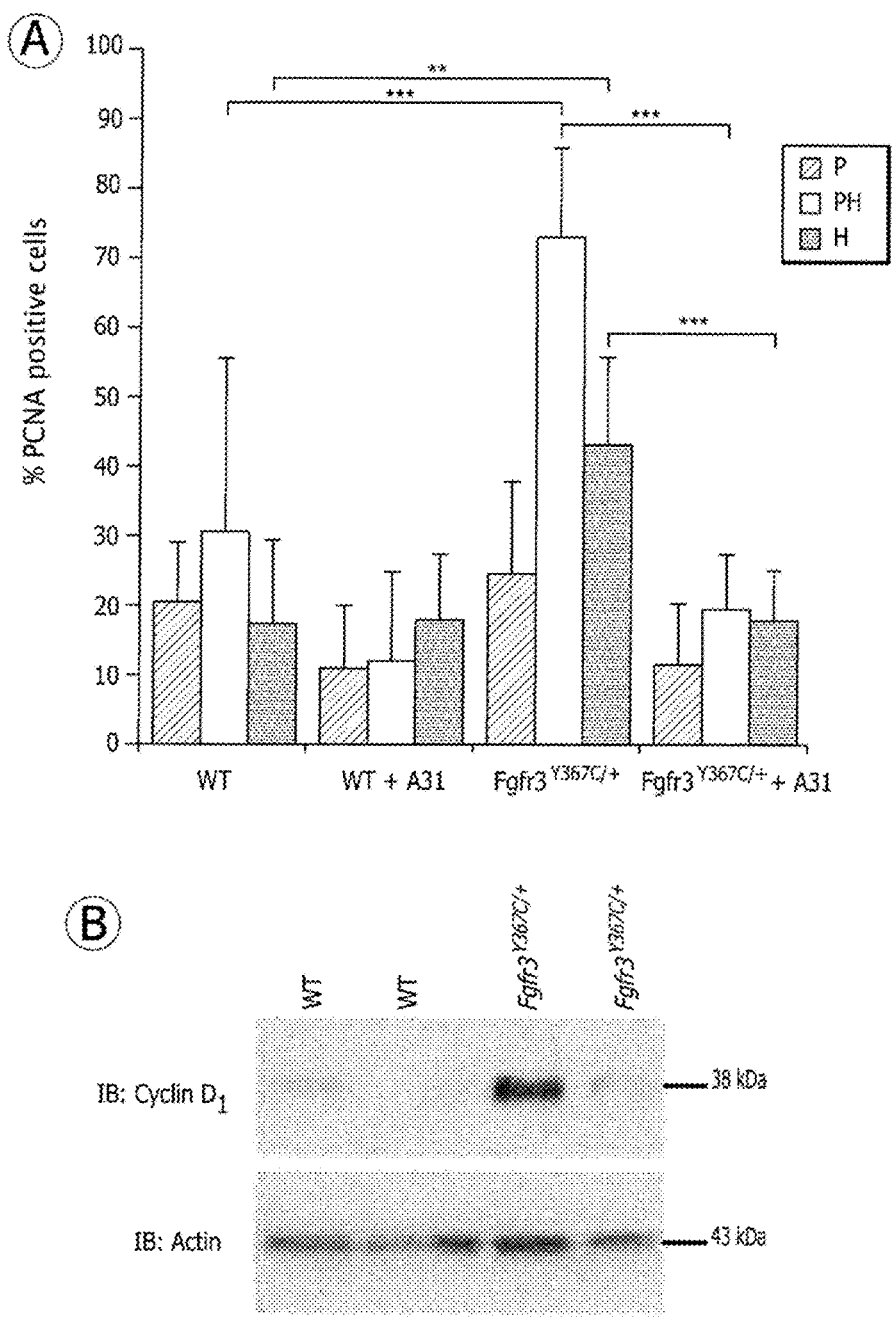

FIG. 6. A31 reduces proliferation and cell cycle regulator expression in growth plates.

(A) Quantification of PCNA-positive cells in proliferative (P), prehypertrophic (PH) and hypertrophic zones (H) showing a higher level of PCNA positive cells in Fgfr3$^{Y367C/+}$ growth plates (73% (PH) and 43% (H), p<0.005 versus WT) compared with WT (31% (PH) and 18% (H)). A31 induces a strong decrease of PCNA expression in PH and H zones of Fgfr3$^{Y357C/+}$ growth plates (20% (PH) and 18% (H), *p<10-4 versus untreated femurs). The experiments were performed six times and three observers counted positive cells. % PCNA positive cells are shown as mean+/−s.d. (B) Immunoblot showing a higher cyclin D1 expression in costal primary Fgfr3$^{Y367C/+}$ chondrocytes compared with WT. A31 reduces the expression of cyclin D1 in Fgfr3$^{Y367C/+}$ chondrocytes. Actin is included as loading control.

FIG. 7. PD173074 restores longitudinal bone growth of Fgfr3Y367C/+ femurs.

(A) Alizarin red and alcian blue staining show that after 5 days of culture PD173074 increases the size of the Fgfr3$^{Y367C/+}$ femurs (left panel). The effect of PD173074 on femur growth is similar to that of A31 (right panel).

(B) PD173074 enhances longitudinal growth in Fgfr3$^{Y367C/+}$ femurs (see bar "PD173074" vs bar "no treatment"), and the bone growth of PD173074 treated femurs is analogous to that observed when Fgfr3$^{Y367C/+}$ femurs are treated with A31.

FIG. 8. PD173074 attenuates the dwarfism phenotype of Fgfr3$^{Y367C/+}$ mice.

Fgfr3$^{Y367C/+}$ mice seven days old received daily subcutaneous administration of 4.00 mg/kg PD173074 for 10 days. Effect of the treatment on the skeleton and body growth was assessed by an X-rays analysis. On panels (A) and (B), PD173074 treated Fgfr3$^{Y367C/+}$ mouse is on the left, vehicle treated Fgfr3$^{Y367C/+}$ mouse is on the right).

Figure 9:
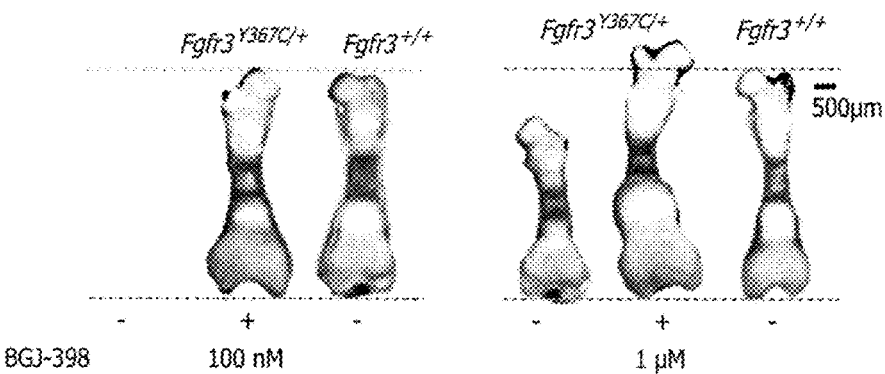

FIG. 9. BGJ-398 restores longitudinal bone growth of Fgfr3Y367C/+ femurs.

Bone length measurements showing a reduced longitudinal growth in Fgfr3$^{Y357C/+}$ femurs compared with WT (Fgfr3$^{+/+}$). Concentration of BGJ-398 ranging from 100 nM to 1 μM enhances longitudinal growth in Fgfr3$^{Y367C/+}$ femurs: the bone growth is greater in Fgfr3$^{Y367C/+}$ femurs compared with controls (Fgfr3$^{+/+}$).

Figure 10:
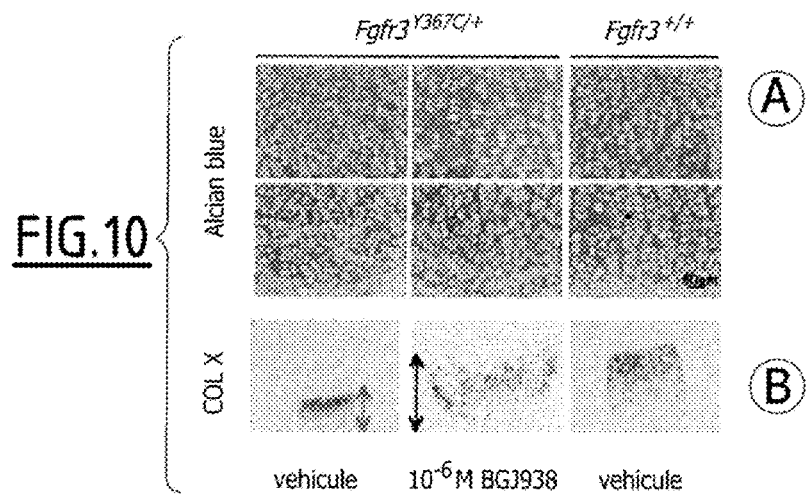

FIG. 10. BGJ-398 modifies the size of the growth plate and chondrocyte morphology.

(A) HES staining showing the reduced size of the Fgfr3$^{Y357C/+}$ growth plate. BGJ-398 induces an increase in the size of the growth plate of the Fgfr3$^{Y367C/+}$ mice. (B) In situ hybridization of type X collagen showing a markedly reduced hypertrophic zone (symbolized by the size of the double-headed arrows) of Fgfr3$^{Y367C/+}$ growth plates compared with WT (Fgfr3$^{+/+}$). BGJ-398 induces enhanced type X collagen expression in Fgfr3$^{Y367C/+}$ growth plates.

Figure 11:

FIG. 11. BGJ-398 attenuates the dwarfism phenotype of Fgfr3$^{Y367C/+}$ mice.

Fgfr3$^{Y367C/+}$ mice seven days old received daily subcutaneous administration of 1.66 mg/kg BGJ-398 for 10 days. Effect of the treatment on the skeleton and body growth was assessed by an X-rays analysis (BGJ-398 treated Fgfr3$^{Y367C/+}$ mouse is on the left, vehicle treated Fgfr3$^{Y367C/+}$ mouse is on the right).

EXAMPLE 1

Materials and Methods

Chemical Compound.

A series of inhibitors was previously designed and synthesized as PD173074 (Miyake et al., J Pharmacol Exp Rher., 332: 797-802, 2010) analogues bearing various N-substituents. Of 27 analogues synthesized, A31 (refers to 19g) was selected in the course of preliminary cellular assays for its ability to inhibit FGFR3 phosphorylation (Le Corre et al., Org Biomol Chem, 8: 2164-2173, 2010.). This compound competes with ATP binding and can inhibit autophosphorylation of FGFR3, with an IC50 value of approximately 190 nM. As a control, the inventors used the commercial FGFR TKI, PD173074. TKIs were dissolved in dimethyl sulfoxide (DMSO) at a concentration of 10 mM. The stock solution was stored at −20° C. before use.

Computational Analyses.

The kinase domain structure of FGFR3 was predicted by homology modelling with the Esypred3D software (Lambert et al., Bioinformatics, 18: 1250-1256, 2002) using a recent X-ray structure of the highly homologous FGFR1 protein (pdb code 3JS2) (Ravindranathan et al., J Med Chem, 53: 1662-1672, 2010). The inventors used AMBER software (Case, D. A., Darden, T. A., Cheatham, T. E., Simmerling, C. L., Wang, J., Duke, R. E., Luo, R., Merz, K. M., Pearlman, D. A., Crowley, M. et al. (2006). University of California, San Francisco) according to a previously published protocol (Luo, Y. et al., J Mol Model, 14: 901-910, 2008). The inventors built A31 compound using the Sybyl software package version 11.0 (SYBYL. Tripos Inc., 1699 South Hanley Rd., St Louis, Mo., 63144 USA). Two states of the asymmetric carbon (R, S) and two different protonation states of the neighboring amino moiety (neutral and +1) were considered. Four distinct chemical structures were obtained. Energy minimizations of these four A31 structures were performed (Hu, R., Barbault, F., Delamar, M. and Zhang, R., Bioorg Med Chem, 17: 2400-2409, 2009). Docking calculations were carried out with version 4.2 of the program AutoDock (Morris et al., J Comput Chem., 19: 1639-1662, 1998.). Kollrnan's united atomic charges were computed. A grid box of 23×20×33 Å was constructed in, respectively, the x, y and z axes around the binding cavity. All ligand torsion angles were allowed to rotate during docking, leading to a complete flexibility. One hundred cycles of calculations of Lamarckian Genetic Algorithm were performed to complete the conformational search. 100 resulting docking structures were clustered into conformation families according to a RMSD lower than 2.0 Å. The inventors selected the conformation, which presented the lowest docking free energy of binding in the most populated cluster.

Ex Vivo Experiments.

Heterozygous Fgfr3$^{Y367C/+}$ mice ubiquitously expressing the Y367C mutation and exhibiting a severe dwarfism were used (Pannier et al., Biochim Biophys Acta, 1792: 140-147, 2009). Six sets of ex vivo experiments were performed. Femur embryos at day E16.5 from WT (n=6) and Fgfr3$^{Y367C/+}$ (n=6) mice were used and incubated for 5 days in DMEM medium with antibiotics and 0.2% BSA (Sigma) supplemented with A31 or PD173074 (as control) at a concentration of 2 mM. Right femur was cultured in supplemented medium and compared with the left one cultured in control medium. Rib cage from E16.5 WT and Fgfr3$^{Y367C/+}$ mice embryos were isolated and stripped of all soft tissues. Primary chondrocytes were obtained from rib cages. The ribs were incubated in a pronase solution (Roche; 2 mg/ml) followed by a digestion in Collagenase A (Roche; 3 mg/ml) at 37° C. Isolated chondrocytes were plated out at a density of 2.105 cells in 6-well plates containing DMEM supplemented with 10% FCS and antibiotics, and were allowed to reach subconfluency. Cultures were supplemented with A31 or PD173074 (as control) at a concentration of 2 mM. Cells were treated with A31 (2 mM) PD173074 (as control) in serum-free DMEM supplemented with 0.2% BSA and harvested after 24 h. To establish the effect of the inhibitors, the right femur was cultured in supplemented medium and compared with the left one cultured in control medium The bone length was measured at the beginning (before treatment) and at the end of time course. Each experiment was repeated at least three times. The genotype of WT, Fgfr3$^{Y357C/+}$ and Fgfr3 mice were determined by PCR of tail DNA as previously described (Pannier et al., Biochim Biophys Acta, 1792: 140-147, 2009). All experimental procedures and protocols were approved by the Animal Care and Use Committee.

Histological, In Situ Hybridization and Immunohistochemical Analyses.

Limb explants were fixed after culture in 4% paraformaldehyde at 4° C., and placed in a staining solution for 45-60 minutes (0.05% Alizarin Red, 0.015% Alcian Blue, 5% acetic acid in 70% ethanol) or embedded in paraffin. Serial mm?sections of 5 were stained with Hematoxylin-Eosin using standard protocols for histological analysis or were subjected to in situ hybridization or immunohistochemical staining.

In situ hybridization using [S35]-UTP labeled antisense ribopropes for collagen X was carried out as previously described (Delezoide et al., Hum Mel Genet, 6, 1899-1906, 1997). Sections were counterstained with Hematoxylin. For immunohistochemistry, sections were stained with antibodies specific to FGFR3 (1:250 dilution; Sigma), anti PCNA (1:1000 dilution; Abcam), anti-KI67 (1:300; Abcam), anti-cyclin D1 (1:80 dilution; Santa Cruz) and anti-p57 (1:100 dilution; Santa Cruz) using the Dako Envision kit. Images were captured with an Olympus PD70-IX2-UCB microscope.

Quantification of PCNA Expression.

Three observers counted PCNA-positive and negative chondrocytes in proliferative (H), prehypertrophic (PH) and hypertrophic (H) zones of the growth plate. A Student's t-test was used to compare treated (A31) and untreated femurs. Imagine software cellSens (Olympus) was used for counting cells. A p-value<0.05 is considered significant.

Immunoprecipitation, Immunoblotting and Immunocytochemistry Experiments.

Human Embryonic Kidney (HEK) cells and human chondrocyte lines (Benoist-Lasselin et al., FEBS Lett, 581: 2593-2598, 2007.) were transfected transiently with FGFR3 human constructs (FGFR3$^{Y373C}$, FGFR3$^{K650M}$, FGFR3$^{K650E}$) (Gibbs, L. and Legeai-Mallet, L. Biochim Biophys Acta, 1773: 502-512, 2007) using Fugene 6 (Roche). A31 (31) or PD173074 (Parke Davies) were added at a concentration of 2 mM overnight. Transfected cells were lysed in RIPA buffer (50 mM Tris-HCl pH 7.6, 150 mM NaCl, 0.5% NP40, 0.25% sodium deoxycholate, supplemented with protease and phosphatase inhibitors).

Immunoprecipitation were performed by incubating 3 mL rabbit anti-FGFR3 (Sigma)/500 mg protein with protein A-agarose (Roche). Immunoprecipitated proteins were subjected to SDS-polyacrylamide gel electrophoresis on NuPAGE 4-12% bis-tris acrylamide gels (Invitrogen). Immunoprecipitated proteins were subjected to SDSpolyacrilamide gels electrophoresis on NuPAGE 4-12% bis-tris acrylamide gels (Invitrogen). Blots were hybridized overnight at 4° C. with anti-FGFR3 polyclonal antibody (1:1,000 dilution; Sigma), or anti-phosphotyrosine monoclonal antibody (1:400 dilution; Cell Signaling). Lysates of primary murine chondrocytes (E16.5) were subjected to SDS-polyacrylamide gel electrophoresis and were hybridized overnight at 4° C. with anti-cyclin D1 monoclonal antibody (1:100 dilution; Santa Cruz). A secondary antibody, anti-rabbit or anti-mouse coupled to peroxidase, was used at a dilution of 1:10,000 (Amersham). Bound proteins were detected by chemiluminescence (ECL, Amersham). The blots were rehybrididized with an antipan-actin antibody for quantification (Millipore).

For immunocytochemistry, the inventors used the following primary antibodies: anti-FGFR3 antibodies (1:400 dilution; Sigma) and anti-phosphotyrosine antibodies (1:200 dilution; Cell Signaling) and secondary antibodies Alexa Fluor®488 goat antirabbit and Alexa Fluor®568 goat antimouse (1:400 dilution; Molecular Probes). Cells were covered with Faramount Aqueous Mounting Medium (Dako) and analyzed using an Olympus PD70-IX2-UCB microscope.

Proliferation Studies.

NIH-3T3 clones stably expressing FGFR3$^{+/+}$ (WT) and FGFR3$^{Y373C}$, FGFR3K650M (human constructs) were used. The stable clones were selected with G418. NIH-3T3 clones were incubated for 8 h in 10% newborn calf serum DMEM supplemented or not with A31 (2 mM). [3H] thymidine was added at a concentration of 10 mCi/ml and incubated for 16 hours. The cells were harvested on glass fiber filter paper and assayed for radioactivity by liquid scintillation counting. The inventors used Top Count Microplates scintillation counter (Perkin Elmer).

In Vivo Experiments.

The effectiveness of PD173074 and BGJ-398 in attenuating the dwarfism phenotype of Fgfr3$^{Y367C/+}$ mice was assessed in vivo. The mice were seven days of age at treatment initiation and received daily subcutaneous administration of 4.00 mg/kg PD173074 or of 1.66 mg/kg BGJ-398 for 10 days.

EXAMPLE 2

Strong Interaction Between the Tyrosine Kinase Domain of FGFR3 and A31

Figure 1:
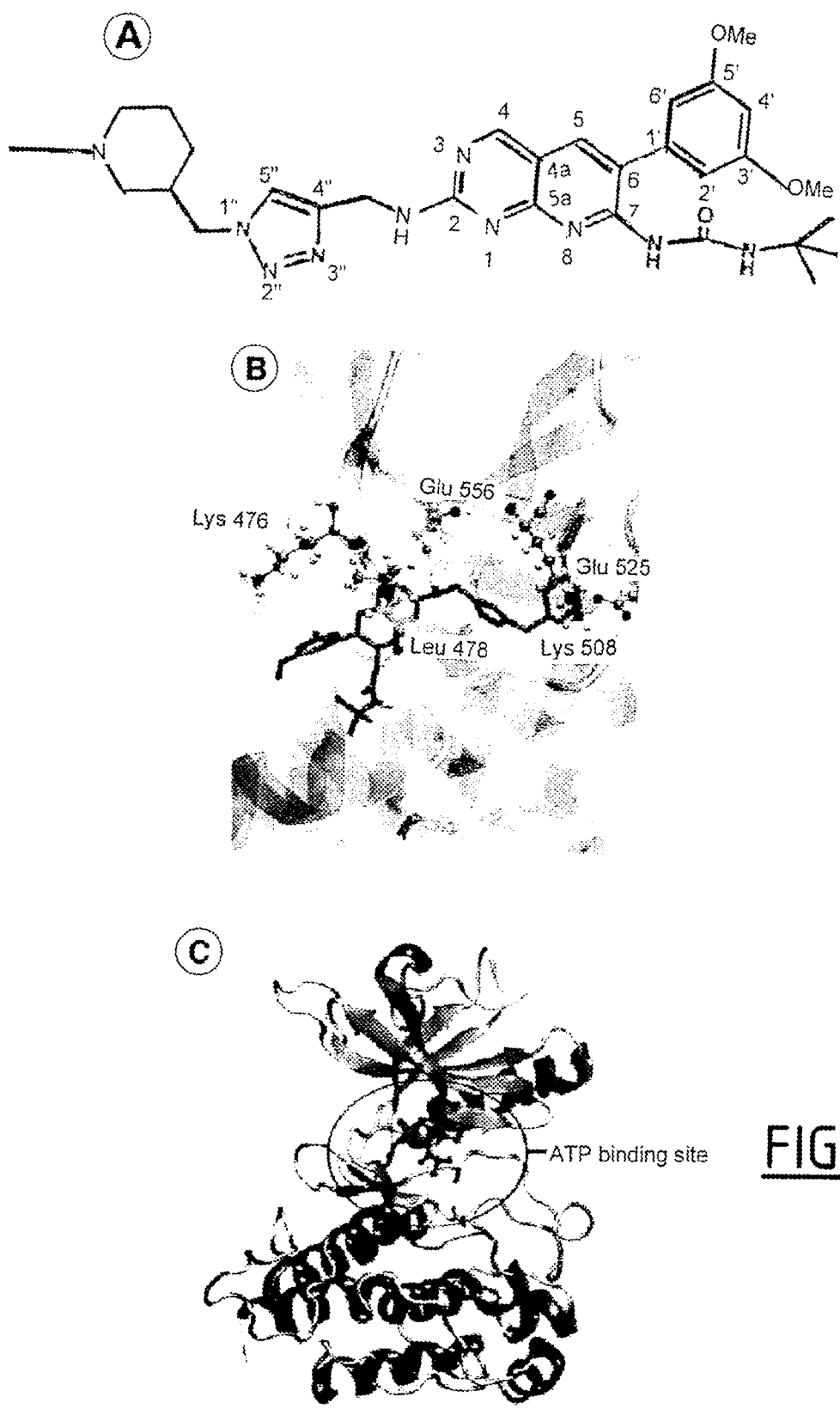
FIG. 1. A31 prevents the kinase activity of FGFR3.

Computational analyses were used to estimate interactions between FGFR3 and A31, a synthetic compound of the pyrido-[2,3-d] pyrimidine class, as a novel FGFR3 tyrosine kinase inhibitor (TKI) (FIG. 1A). To date, attempts to determine the experimental Xray structure of the FGFR3 kinase domain have failed. To overcome this drawback, the inventors predicted the structure of FGFR3 in silico by using a new crystal structure of the highly homologous FGFR1 (Ravindranathan et al., J Med Chem, 53: 1662-1672, 2010).

The resulting 3D structure of FGFR3 showed a low global energy and negative electrostatic and Van der Waals components indicating a high level of confidence for this prediction. Docking calculations were used to find the optimal position of A31 in the binding pocket of FGFR3. The interactions between the FGFR3 kinase domain and A31 are depicted in FIG. 1B. The aromatic group carrying the two methoxy moieties and the biphenyl ring induce strong interactions between the FGFR3 kinase domain and A31. Two hydrogen bonds locate the biphenyl ring at the adenine position of ATP, filling the FGFR3 active site and in this way, A31 competes directly with the substrate. The cyclic amino tail of A31 is deeply nestled inside the FGFR3 cavity in the vicinity of a protein salt bridge. As a consequence, the salt bridge is disrupted, thus preventing the kinase activity of FGFR3. These in-silico data suggest that A31 specifically inhibits FGFR3 kinase activity.

EXAMPLE 3

A31 Inhibits FGFR3 Phosphorylation and Proliferation of Mutant Fgfr3 Cell Lines The inventors evaluated the ability of A31 to inhibit the constitutive phosphorylation of FGFR3 in human chondrocyte lines (Gibbs, L. and Legeai-Mallet, L. Biochim Biophys Acta, 1773: 502-512, 2007) transiently expressing activated forms of FGFR3 (FGFR3$^{Y373C}$ or FGFR3$^{K650E}$ (TD), FGFR3$^{K650M}$ (SADDAN) or FGFR3$^{+/+}$).

Immunoprecipitation and Western blotting showed the presence of a 130 kDa mature isoform in the WT and FGFR3$^{Y373C}$ cell lysates, whereas only an 115 kDa immature form was present in FGFR3$^{K650M}$ and FGFR3$^{K650E}$ lysates (FIG. 2). A31, abolished receptor phosphorylation in all cells expressing FGFR3 mutations (FIG. 2). Similar results were found with a commercial TKI inhibitor (PD173074) (FIG. 2). This inhibition was confirmed by immunocytochemistry in transfected cells expressing FGFR3 mutations (data not shown). The inventors observed a complete inhibition of FGFR3 phosphorylation by A31.

This data confirmed the ability of A31 to inhibit constitutive FGFR3 phosphorylation in transfected cells. To determine whether A31 modulates the mitogenic activity of activated FGFR3, the inventors measured [3H]-thymidine incorporation in FGFR3$^{Y373C}$ and FGFR3$^{K650M}$ transfected NIH3T3 cells. The mitogenic activity was increased in cells expressing FGFR3 mutations compared to WT (FGFR3$^{Y373C}$, 9927±2921 cpm; FGFR3$^{K650M}$, 15048±5251 cpm; WT, 7499±1667 cpm; p<10$^{-5}$ versus WT).

A31 treatment strongly reduced DNA synthesis of all mutant cell lines (FGFR3$^{Y373C}$, 3144±1201 cpm; FGFR3$^{K650M}$, 6281±2699 cpm; p<10$^{-10}$, *p<10$^{-20}$ versus DMSO). These results demonstrate that A31 decreases the mitogenic activity of FGFR3 mutants.

To confirm these results, the ability of BGJ-398 (also designated as compound 1 h in Table B), another tyrosine kinase inhibitor, to inhibit the constitutive phosphorylation of FGFR3 in cells (HEK-293) transiently expressing activated forms of FGFR3 (i.e. FGFR3Y373C, FGFR3K650E, FGFR3K650M, FGFR3G380R) was also tested. It was found that 10 μM of BGJ-398 abolished receptor phosphorylation in all cells expressing FGFR3 mutations (data not shown).

EXAMPLE 4

Rescue of the Fgfr3$^{Y367C/+}$ Femur Growth Defect by A31 and BGJ-398

A31 was tested on a gain of function Fgfr3$^{Y367C/+}$ mouse model (Pannier et al., Biochim Biophys Acta, 1792: 140-147, 2009). It is to be noted that mutation Y367C in mouse FGFR3 corresponds to mutation Y373C in human FGFR3.

Fgfr3$^{Y367C/+}$ mice display reduced length of long bones, broad femurs, a narrow trunk, short ribs and a slightly dome-shaped skull, closely resembling achondroplasia (FIGS. 3A and B). The inventors analyzed the effects of A31 on endochondral ossification in Fgfr3$^{Y367C/+}$ mice by using an ex vivo culture system for embryonic day 16.5 (E16.5) limb explants. Mutant femurs cultured without A31 had a significantly reduced longitudinal growth compared to WT (Fgfr3$^{Y367C/+}$, 461±119 μm; WT, 1247±226 μm; p<10$^{-10}$) (FIGS. 3C and D). A31 was able to induce and fully restore limb growth in Fgfr3$^{Y367C/+}$ femurs (Fgfr3$^{Y367C/+}$, gain of 1880±558 μm; WT, 1863±255 μm; p<10$^{-19}$) (FIGS. 3C and D). After 5 days of culture, the increase in length of the treated mutant femurs was 2.6 times more than for that of WT.

Histological examinations using HES staining (FIG. 4A) and type X collagen labeling (FIG. 4B), revealed a reduction in size of the hypertrophic zone of the Fgfr3$^{Y357C/+}$ mouse growth plate (FIG. 4B), with abnormally small chondrocytes resembling prehypertrophic rather than hypertrophic cells. The inventors evaluated the impact of A31 on the growth plate (FIG. 4A). Interestingly, A31 induced a marked expansion of the hypertrophic zone, with marked modifications of the shape of proliferative and hypertrophic cells. A31-treated chondrocytes appeared enlarged and more spherical, resembling to hypertrophic chondrocytes (data not shown). Therefore, these results suggest that A31 increased the size of mutant growth plates by restoring the disrupted chondrocyte maturation process.

To confirm the results obtained with tyrosine kinase inhibitor "A31", another FGFR3 belonging to the pyrido[2,3-d]pyrimidine class, i.e. the tyrosine kinase inhibitor "PD173074", was also tested.

Thus, embryonic femur explants were co-incubated with 150 nM of PD173074 for 5 days.

As illustrated by the gain in femur length, PD173074 for 5 days is sufficient for correcting the difference in length and normalized the size of the epiphyses PD173074 enhances longitudinal growth in Fgfr3$^{Y367C/+}$ femurs (gain of 77%; see FIGS. 7 (A) and (B); mutant femurs cultured without PD173074 had a reduced longitudinal growth compared to WT femurs (Fgfr3$^{+/+}$). The effect of PD173074 on femur growth is similar to that of A31 (see FIGS. 7 (A) and (B)).

Similar experiments were conducted with an antagonist which belongs to the N-aryl-N-pyrimidin-4-yl urea class, i.e. the tyrosine kinase inhibitor "BGJ-398".

Embryonic femur explants were co-incubated 100 nM (10$^7$M) or 1 μM (10$^{-6}$M) of BGJ-398 for 6 days.

A concentration-dependent increase in femur size was observed for BGJ-398 concentrations ranging from 100 nM to 1 μM, as illustrated by the gain in femur length. 100 nM of BGJ-398 for 6 days is sufficient for correcting the difference in length and normalized the size of the epiphyses. A gain of 71.86% is observed in treated Fgfr3$^{Y367C/+}$ femurs (FIG. 9; mutant femurs cultured without BGJ-398 had a reduced longitudinal growth compared to WT femurs (Fgfr3$^{+/+}$).

Histological examinations using HES staining (FIG. 10A) and type X collagen labeling (FIG. 10B) were also carried out.

HES staining of WT (Fgfr3$^{+/+}$) and Fgfr3$^{Y367C/+}$ mice showed that growth plate from Fgfr3$^{Y367C/+}$ mice have smaller mutant chondrocytes, whereas cells are larger and more spherical when femurs are cultured in the presence of 10$^{-6}$M of BGJ-398 (FIG. 10A).

FIG. 10B shows that BGJ-398 induces enhanced type X collagen expression in Fgfr3$^{Y367C/+}$ growth plate and that the size of the hypertrophic zone of the femur explants of Fgfr3$^{Y367C/+}$ mice increases.

Taken together, these results showed histological changes (increased chondrocyte proliferation and differentiation) when femurs from Fgfr3$^{Y367C/+}$ mice are cultivated in the presence of BGJ-398.

EXAMPLE 5

Effect of A31 on Fgfr3 Protein Expression

The inventors evaluated the level of Fgfr3 protein expression by immunohistochemical staining and found an overexpression of Fgfr3 in Fgfr3$^{Y367C/+}$ growth plates. A31 induced a large decrease of Fgfr3 expression in mutant femurs (data not shown). These results were confirmed by Western blotting on primary chondrocytes isolated from E16.5 ribs (FIG. 5). A higher level of Fgfr3 was revealed in untreated Fgfr3$^{Y367C/+}$ chondrocytes, whereas this level was similar to WT after addition of A31. These data indicate that inhibition of the constitutive phosphorylation of Fgfr3 by A31 rescues the turnover of the receptor.

EXAMPLE 6

A31 Modulates the Expression of Cell Cycle Regulator Genes

Analysis of expression of Proliferating Cell Nuclear Antigen (PCNA), an Sphase marker, revealed abnormally high levels of PCNA in the prehypertrophic (PH) (73% of total cells positive; $p<0.005$) and hypertrophic (H) areas of Fgfr3$^{Y367C/+}$ mouse growth plates (43% of total cells positive; $p<0.005$). A31 strongly decreased PCNA expression in the corresponding areas of mutant growth plates (20% and 18% for PH and H areas, respectively, ***$p<10^4$) (FIG. 6A). Likewise, higher expression levels of KI67 were observed in the PH and H areas of Fgfr3$^{Y367C/+}$ mouse growth plates compared to controls (data not shown). A31 also decreased this expression in Fgfr3$^{Y367C/+}$ mouse growth plates (data not shown). The inventors noted a higher expression of PCNA than K167 in the mutant growth plate. Furthermore, the inventors investigated whether the presence of mutated Fgfr3 caused an impairment of expression of cell cycle regulators. In fact, activated Fgfr3 induced a significant overexpression of cyclin D1 in the proliferative and PH chondrocytes of Fgfr3$^{Y367C/+}$ mice. Interestingly, A31 returned cyclin D1 expression to control levels in mutant femurs (data not shown). Consistent with this Western blots showed a reduced level of cyclin D1 in A31-treated murine chondrocytes isolated from E16.5 ribs compared to untreated chondrocytes (FIG. 6B). The inventors further analyzed the level of CDK inhibitors (CDKIs) negatively regulating the cell cycle, particularly p57, a member of the Cip/Kip family. Activated Fgfr3 induced a higher expression of p57 predominantly in late proliferative and PH chondrocytes. A31 reduced expression of p57 protein particularly in the PH zone and enabled PH chondrocytes to properly differentiate into H chondrocytes (data not shown). The inventors conclude that activated FGFR3 leads to overexpression of markers of proliferation (PCNA, KI67) and cell cycle regulators (cyclin D1 and p57) particularly in the prehypertrophic zone. These data highlight the dysregulation of the cell cycle in this skeletal pathology.

EXAMPLE 7

Effect of PD173074 in a Dwarfism Mouse Model

The effectiveness of PD173074 in attenuating the dwarfism phenotype of Fgfr3$^{Y367C/+}$ mice was assessed in vivo. The mice were seven days of age at treatment initiation and received daily subcutaneous administrations of 4.00 mg/kg of PD173074 for 10 days.

Results of this experiment are disclosed in FIG. 8 which is an X-rays analysis of Fgfr3$^{Y367C/+}$ mice administered with PD173074 or with a vehicle ("mock" experiment). Amelioration in key relevant achondroplasia clinical features including bowed femur and tibia, anterior crossbite and domed skull was observed (see FIGS. 8A and B; compare PD173074-treated mouse on the left side of panels A and B vs vehicle-administered mouse on the right side of panels A and B). Indeed, dramatic phenotypic changes are observed, including larger paws and digits, and longer and straightened tibia and femurs in Fgfr3$^{Y367C/+}$ mouse treated with PD173074.

Therefore, improvement in the dwarfism was obvious after 10 days of treatment in animals given 4.00 mg/kg PD173074 and included an overall increase in body size with longer tail and snout.

EXAMPLE 8

Effect of BGJ-398 in a Dwarfism Mouse Model

Seven days old mice received daily subcutaneous administrations of 1.66 mg/kg of BGJ-398 for 10 days.

Dramatic phenotypic changes are observed, including larger paws and digits, and longer and straightened tibia and femurs in Fgfr3$^{Y367C/+}$ mouse treated with BGJ-398 (see FIG. 11 which is an X-rays of Fgfr3$^{Y367C/+}$ mice administered with BGJ-398—mouse on the left side of the figure—or with a vehicle ("mock" experiment)—mouse on the right side of the figure).

The invention claimed is:
1. A method for treating a FGFR3-related skeletal disease which comprises the step of administering a therapeutically effective amount of at least one antagonist of the FGFR3 tyrosine kinase receptor of formula:

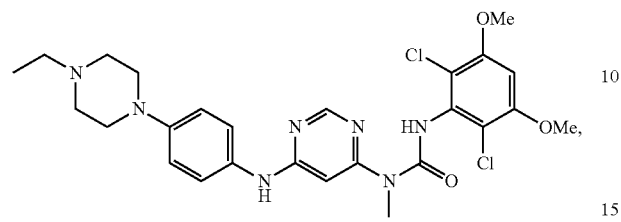

or a composition comprising such an antagonist, to a subject in need thereof, and treating the FGFR3-related skeletal disease in said subject, wherein the FGFR3-related skeletal disease is achondroplasia.

* * * * *

UNITED STATES PATENT AND TRADEMARK OFFICE
CERTIFICATE OF CORRECTION

PATENT NO. : 9,931,341 B2
APPLICATION NO. : 14/844041
DATED : April 3, 2018
INVENTOR(S) : Laurence Legeai-Mallet et al.

It is certified that error appears in the above-identified patent and that said Letters Patent is hereby corrected as shown below:

On the Title Page

Foreign priority number should read: PCT/IB2011/003253

Signed and Sealed this
Twenty-eighth Day of December, 2021

Drew Hirshfeld
*Performing the Functions and Duties of the*
*Under Secretary of Commerce for Intellectual Property and*
*Director of the United States Patent and Trademark Office*